United States Patent [19]
Cerletti et al.

[11] Patent Number: 5,650,494
[45] Date of Patent: Jul. 22, 1997

[54] PROCESS FOR REFOLDING RECOMBINANTLY PRODUCED TGF-β-LIKE PROTEINS

[75] Inventors: Nico Cerletti, Bottmingen; Gary Kent McMaster, Kaiseraugst; David Cox, Himmelried; Albert Schmitz, Basel; Bernd Meyhack, Magden, all of Switzerland

[73] Assignee: Ciba-Geigy Corporation, Tarrytown, N.Y.

[21] Appl. No.: 486,057

[22] Filed: Jun. 7, 1995

Related U.S. Application Data

[63] Continuation of Ser. No. 201,703, Feb. 25, 1994, abandoned, which is a continuation of Ser. No. 960,309, Oct. 13, 1992, abandoned, which is a continuation of Ser. No. 621,502, Dec. 3, 1990, abandoned.

[30] Foreign Application Priority Data

Dec. 6, 1989 [GB] United Kingdom ............... 8927546

[51] Int. Cl.$^6$ ............... C07K 1/14; C07K 14/495; C12P 21/04
[52] U.S. Cl. ............... 530/399; 530/427; 435/69.4; 435/71.2
[58] Field of Search ............... 530/350, 351, 530/399, 427; 435/69.1, 69.4, 71.1, 71.2

[56] References Cited

U.S. PATENT DOCUMENTS

| | | | |
|---|---|---|---|
| 4,620,948 | 11/1986 | Builder et al. | 530/419 |
| 4,742,003 | 5/1988 | Derynck et al. | 530/350 |
| 5,162,507 | 11/1992 | Wolfe et al. | 530/412 |
| 5,453,363 | 9/1995 | Rudolph et al. | 435/69.1 |

FOREIGN PATENT DOCUMENTS

| | | |
|---|---|---|
| 0114506 | 12/1983 | European Pat. Off. . |
| 0200341 | 12/1986 | European Pat. Off. . |
| 0267463 | 5/1988 | European Pat. Off. . |
| 0268561 | 5/1988 | European Pat. Off. . |
| 0293785 | 12/1988 | European Pat. Off. . |
| 86/05809 | 10/1986 | WIPO . |
| 8808003 | 10/1988 | WIPO . |
| 8808849 | 11/1988 | WIPO . |

OTHER PUBLICATIONS

Chan, Biochemistry, vol. 7, No. 12 pp. 4247–4254, (1968).
Reeck et al, (1987) Cell, 50, 667.
King (30 Apr. 1989) Chem. Eng. News, 32–54.
Lewin (1987) Science, 237, 1570.
Boswell et al. (1988) "Computational Molecular Biology", A.M. Lesk, Ed., Oxford Press, New York.
Hoppe et al., Biochemistry, 28:2956–2960 (1989).
Hjelmeland et al., (1983) Anal. Biochem. 130: 72–82.
Hjelmeland et al., (1984) Methods Enzymol. 104: 305–318.
Helenius et al., (1979) Methods Enymol. LVI: 734–749.
Ten Dijke et al., (1988) Proc. Natl. Acad. Sci USA 85: 4715–4719.
Derynk et al., (1988) Embo J. 7(12): 3737–3743.
Takuwa et al., (1989) Biochem. Biophys. Res. Comm. 174:96.
Absher et al., "A rapid colorimetric bioassay for transforming growth factor β (TFG-β) using a microwell plate reader", Journal of Immunological Methods, 138:301–303 (1991).
Creighton, T.E., "[19] Disulfide Bond Formation in Proteins", Methods in Enzymology, 107:305–329 (1984).
Danielpour et al., "Immunodetection and Quantitation of the Two Forms of Transforming Growth Factor–Beta (TFG-β1 and TGF-β2) Secreted by Cells in Culture", Journal of Cellular Physiology, 138:79–86 (1989).
Kelley et al., "Complex Cytokine Modulation of a Continuous Line of Mink Lung Epithelial Cells (Mv1LU)", Experimental Lung Research, 18:877–887 (1992).
Meager, A., "Asssays for transforming growth factor β", Journal of Immunological Methods, 141:1–14 (1991).
Takuwa et al., "Bone Morphogenetic Protein-2 Stimulates Alkaline Phosphatase Activity and Collagen Synthesis in Cultured Osteoblastic Cells, MC3T3-E1", Department of Internal Medicine, Institute of Clinical Medicine, University of Tsukuba, Tsukuba, Ibaraki 305, Japan, 96–101 (1991).
Tucker et al., "Growth Inhibitor from BSC-1 Cells Closely Related to Platelet Type β Transforming Growth Factor", Science, 226:705–707 (1984).
Wozney et al., "Novel Regulators of Bone Formation: Molecular Clones and Activities", Science, 242:1528–1534 (1988).
Ahmed, A.K., et al., "Nonenzymic Reactivation of Reduced Bovine Pancreatic Ribonuclease by Air Oxidation and by Gluthathione Oxidoreduction Buffers", J. Biol. Chem., 250(21):8477–8482 (1975).

(List continued on next page.)

Primary Examiner—David M. Naff
Assistant Examiner—Jon P. Weber
Attorney, Agent, or Firm—Henry P. Nowak

[57] ABSTRACT

The process for the production of a dimeric, biologically active Transforming Growth Factor type β (TGF-β)-like protein or a salt thereof, comprising refolding the denatured monomeric form of the protein in the presence of a mild detergent that permits folding of the monomeric protein into a spatial conformation, which after dimerization, is the conformation associated with the biological activity, while retaining the monomeric protein in soluble form. Mild detergents include sulfobetaines, 3-(3-chlolamidopropyl) dimethylammonio-1-propanesulfonate, 3-(3-chlolamidopropyl)dimethylammonio-2-hydroxy-1-propane-sulfonate, digitonin, cholate and deoxycholate at a concentration of about 1 to 100 mM. Compositions containing a TGF-β-like protein produced according the invention can be used for the promotion and acceleration of wound healing and bone and tissue repair, cancer treatment, bone marrow protective agent, as a mediator of cardio-protection, as an anti-inflammatory or immunosuppressive agent, or as a growth regulator in mammalian cell cultures.

30 Claims, No Drawings

OTHER PUBLICATIONS

Tandon, S., et al., "Detergent–assisted Refolding of Guanidinium Chloride–denatured Rhodanese: The Effect of Lauryl Maltoside", *J. Biol. Chem.*, 261(33):15615–15681 (1986).

Tandon, S., et al., "Detergent–assisted Refolding of Guanidinium Chloride–denatured Rhodanese: The Effects of the Concentration and Type of Detergent", *J. Biol. Chem.*, 262(10):4486–4491 (1987).

Tandon, S., et al., "The Effects of Lauryl Maltoside on the Reactivation of Several Enzymes after Treatment with Guanidinium Chloride", *Biochim. Biophys. Acta.*, 955:19–25 (1988).

Tandon, S. et al., "Reversible Folding of Rhodanese: Presence of Intermediate(s) at Equilibrium", *J. Biol. Chem.*, 264(17):9859–9866 (1989).

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 339 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
    ( A ) NAME/KEY: CDS
    ( B ) LOCATION: 1..339

( i x ) FEATURE:
    ( A ) NAME/KEY: CDS
    ( B ) LOCATION: 1..339

( x i ) SEQUENCE DESCRIPTION: SEQ ID NO:1:

| GCC | CTG | GAC | ACC | AAC | TAT | TGC | TTC | AGC | TCC | ACG | GAG | AAG | AAC | TGC | TGC | 48 |
|---|---|---|---|---|---|---|---|---|---|---|---|---|---|---|---|---|
| Ala | Leu | Asp | Thr | Asn | Tyr | Cys | Phe | Ser | Ser | Thr | Glu | Lys | Asn | Cys | Cys | |
| 1 | | | | 5 | | | | | 10 | | | | | 15 | | |

| GTG | CGG | CAG | CTG | TAC | ATT | GAC | TTC | CGC | AAG | GAC | CTC | GGC | TGG | AAG | TGG | 96 |
|---|---|---|---|---|---|---|---|---|---|---|---|---|---|---|---|---|
| Val | Arg | Gln | Leu | Tyr | Ile | Asp | Phe | Arg | Lys | Asp | Leu | Gly | Trp | Lys | Trp | |
| | | | 20 | | | | | 25 | | | | | 30 | | | |

| ATC | CAC | GAG | CCC | AAG | GGC | TAC | CAT | GCC | AAC | TTC | TGC | CTC | GGG | CCC | TGC | 144 |
|---|---|---|---|---|---|---|---|---|---|---|---|---|---|---|---|---|
| Ile | His | Glu | Pro | Lys | Gly | Tyr | His | Ala | Asn | Phe | Cys | Leu | Gly | Pro | Cys | |
| | | 35 | | | | | 40 | | | | | 45 | | | | |

| CCC | TAC | ATT | TGG | AGC | CTG | GAC | ACG | CAG | TAC | AGC | AAG | GTC | CTG | GCC | CTG | 192 |
|---|---|---|---|---|---|---|---|---|---|---|---|---|---|---|---|---|
| Pro | Tyr | Ile | Trp | Ser | Leu | Asp | Thr | Gln | Tyr | Ser | Lys | Val | Leu | Ala | Leu | |
| | 50 | | | | | 55 | | | | | 60 | | | | | |

| TAC | AAC | CAG | CAT | AAC | CCG | GGC | GCC | TCG | GCG | GCG | CCG | TGC | TGC | GTG | CCG | 240 |
|---|---|---|---|---|---|---|---|---|---|---|---|---|---|---|---|---|
| Tyr | Asn | Gln | His | Asn | Pro | Gly | Ala | Ser | Ala | Ala | Pro | Cys | Cys | Val | Pro | |
| 65 | | | | | 70 | | | | | 75 | | | | | 80 | |

| CAG | GCG | CTG | GAG | CCG | CTG | CCC | ATC | GTG | TAC | TAC | GTG | GGC | CGC | AAG | CCC | 288 |
|---|---|---|---|---|---|---|---|---|---|---|---|---|---|---|---|---|
| Gln | Ala | Leu | Glu | Pro | Leu | Pro | Ile | Val | Tyr | Tyr | Val | Gly | Arg | Lys | Pro | |
| | | | | 85 | | | | | 90 | | | | | 95 | | |

| AAG | GTG | GAG | CAG | CTG | TCC | AAC | ATG | ATC | GTG | CGC | TCC | TGC | AAG | TGC | AGC | 336 |
|---|---|---|---|---|---|---|---|---|---|---|---|---|---|---|---|---|
| Lys | Val | Glu | Gln | Leu | Ser | Asn | Met | Ile | Val | Arg | Ser | Cys | Lys | Cys | Ser | |
| | | | 100 | | | | | 105 | | | | | 110 | | | |

| TGA | | | | | | | | | | | | | | | | 339 |
|---|---|---|---|---|---|---|---|---|---|---|---|---|---|---|---|---|
| * | | | | | | | | | | | | | | | | |

( 2 ) INFORMATION FOR SEQ ID NO:2:

( i ) SEQUENCE CHARACTERISTICS:
        ( A ) LENGTH: 339 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..339

( x i ) SEQUENCE DESCRIPTION: SEQ ID NO:2:

| GCT | TTG | GAT | GCG | GCC | TAT | TGC | TTT | AGA | AAT | GTG | CAG | GAT | AAT | TGC | TGC | 48 |
|---|---|---|---|---|---|---|---|---|---|---|---|---|---|---|---|---|
| Ala | Leu | Asp | Ala | Ala | Tyr | Cys | Phe | Arg | Asn | Val | Gln | Asp | Asn | Cys | Cys | |
| 115 | | | | | 120 | | | | | 125 | | | | | | |

| CTA | CGT | CCA | CTT | TAC | ATT | GAT | TTC | AAG | AGG | GAT | CTA | GGG | TGG | AAA | TGG | 96 |
|---|---|---|---|---|---|---|---|---|---|---|---|---|---|---|---|---|
| Leu | Arg | Pro | Leu | Tyr | Ile | Asp | Phe | Lys | Arg | Asp | Leu | Gly | Trp | Lys | Trp | |
| 130 | | | | | 135 | | | | | 140 | | | | | 145 | |

| ATA | CAC | GAA | CCC | AAA | GGG | TAC | AAT | GCC | AAC | TTC | TGT | GCT | GGA | GCA | TGC | 144 |
|---|---|---|---|---|---|---|---|---|---|---|---|---|---|---|---|---|
| Ile | His | Glu | Pro | Lys | Gly | Tyr | Asn | Ala | Asn | Phe | Cys | Ala | Gly | Ala | Cys | |
| | | | | 150 | | | | | 155 | | | | | 160 | | |

| CCG | TAT | TTA | TGG | AGT | TCA | GAC | ACT | CAG | CAC | AGC | AGG | GTC | CTG | AGC | TTA | 192 |
|---|---|---|---|---|---|---|---|---|---|---|---|---|---|---|---|---|
| Pro | Tyr | Leu | Trp | Ser | Ser | Asp | Thr | Gln | His | Ser | Arg | Val | Leu | Ser | Leu | |
| | | | 165 | | | | | 170 | | | | | 175 | | | |

| TAT | AAT | ACC | ATA | AAT | CCA | GAA | GCA | TCT | GCT | TCT | CCT | TGC | TGC | GTG | TCC | 240 |
|---|---|---|---|---|---|---|---|---|---|---|---|---|---|---|---|---|
| Tyr | Asn | Thr | Ile | Asn | Pro | Glu | Ala | Ser | Ala | Ser | Pro | Cys | Cys | Val | Ser | |
| | | 180 | | | | | 185 | | | | | 190 | | | | |

| CAA | GAT | TTA | GAA | CCT | CTA | ACC | ATT | CTC | TAC | TAC | ATT | GGC | AAA | ACA | CCC | 288 |
|---|---|---|---|---|---|---|---|---|---|---|---|---|---|---|---|---|
| Gln | Asp | Leu | Glu | Pro | Leu | Thr | Ile | Leu | Tyr | Tyr | Ile | Gly | Lys | Thr | Pro | |

|  |  |  |  |  |  |  |  |  |  |  |  |  |  |  |
|---|---|---|---|---|---|---|---|---|---|---|---|---|---|---|
|  |  | 195 |  |  |  | 200 |  |  |  |  | 205 |  |  |  |
| AAG | ATT | GAA | CAG | CTT | TCT | AAT | ATG | ATT | GTA | AAG | TCT | TGC | AAA | TGC | AGC | 336 |
| Lys | Ile | Glu | Gln | Leu | Ser | Asn | Met | Ile | Val | Lys | Ser | Cys | Lys | Cys | Ser |
| 210 |  |  |  |  | 215 |  |  |  |  | 220 |  |  |  |  | 225 |

TAA     339
*

( 2 ) INFORMATION FOR SEQ ID NO:3:

( i ) SEQUENCE CHARACTERISTICS:
        ( A ) LENGTH: 339 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..339

( x i ) SEQUENCE DESCRIPTION: SEQ ID NO:3:

| GCT | TTG | GAC | ACC | AAT | TAC | TGC | TTC | CGC | AAC | TTG | GAG | GAG | AAC | TGC | TGT | 48 |
|---|---|---|---|---|---|---|---|---|---|---|---|---|---|---|---|---|
| Ala | Leu | Asp | Thr | Asn | Tyr | Cys | Phe | Arg | Asn | Leu | Glu | Glu | Asn | Cys | Cys |
| 115 |  |  |  |  | 120 |  |  |  |  | 125 |  |  |  |  |  |
| GTG | CGC | CCC | CTC | TAC | ATT | GAC | TTC | CGA | CAG | GAT | CTG | GGC | TGG | AAG | TGG | 96 |
| Val | Arg | Pro | Leu | Tyr | Ile | Asp | Phe | Arg | Gln | Asp | Leu | Gly | Trp | Lys | Trp |
| 130 |  |  |  |  | 135 |  |  |  |  | 140 |  |  |  |  | 145 |
| GTC | CAT | GAA | CCT | AAG | GGC | TAC | TAT | GCC | AAC | TTC | TGC | TCA | GGC | CCT | TGC | 144 |
| Val | His | Glu | Pro | Lys | Gly | Tyr | Tyr | Ala | Asn | Phe | Cys | Ser | Gly | Pro | Cys |
|  |  |  |  | 150 |  |  |  |  | 155 |  |  |  |  | 160 |  |
| CCA | TAC | CTC | CGC | AGT | GCA | GAC | ACA | ACC | CAC | AGC | ACG | GTG | CTG | GGA | CTG | 192 |
| Pro | Tyr | Leu | Arg | Ser | Ala | Asp | Thr | Thr | His | Ser | Thr | Val | Leu | Gly | Leu |
|  |  |  | 165 |  |  |  |  | 170 |  |  |  |  | 175 |  |  |
| TAC | AAC | ACT | CTG | AAC | CCT | GAA | GCA | TCT | GCC | TCG | CCT | TGC | TGC | GTG | CCC | 240 |
| Tyr | Asn | Thr | Leu | Asn | Pro | Glu | Ala | Ser | Ala | Ser | Pro | Cys | Cys | Val | Pro |
|  |  | 180 |  |  |  |  | 185 |  |  |  |  | 190 |  |  |  |
| CAG | GAC | CTG | GAG | CCC | CTG | ACC | ATC | CTG | TAC | TAT | GTT | GGG | AGG | ACC | CCC | 288 |
| Gln | Asp | Leu | Glu | Pro | Leu | Thr | Ile | Leu | Tyr | Tyr | Val | Gly | Arg | Thr | Pro |
| 195 |  |  |  |  | 200 |  |  |  |  | 205 |  |  |  |  |  |
| AAA | GTG | GAG | CAG | CTC | TCC | AAC | ATG | GTG | GTG | AAG | TCT | TGT | AAA | TGT | AGC | 336 |
| Lys | Val | Glu | Gln | Leu | Ser | Asn | Met | Val | Val | Lys | Ser | Cys | Lys | Cys | Ser |
| 210 |  |  |  |  | 215 |  |  |  |  | 220 |  |  |  |  | 225 |

TGA     339
*

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GCCCTGGACA CCAACTATTG CTTCAGCTCC ACGGAGAAG     39

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:5:

TCAGCTGCAC TTGCAGGAGC GCACGATCAT GTTGGACAG     39

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:6:

GCTTTGGATG CGGCCTATTG CTTTAGAAAT GTGCAGGAT     39

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:7:

TTAGCTGCAT TTGCAAGACT TTACAATCAT ATTAGAAAG     39

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:8:

GCTTTGGACA CCAATTACTG CTTCCGCAAC TTGGAGGAG     39

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:9:

TCAGCTACAT TTACAAGACT TCACCACCAT GTTGGAGAG     39

(2) INFORMATION FOR SEQ ID NO:10:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: unknown (i i) MOLECULE TYPE: peptide (x i) SEQUENCE DESCRIPTION: SEQ ID NO:10:

```
Ala Leu Asp Ala Ala Tyr Xaa Phe Arg Asn Val Gln Asp Asn Xaa Xaa
1               5                   10                  15

Leu Arg Pro
```

(2) INFORMATION FOR SEQ ID NO:11:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:11:

```
Ala Leu Asp Ala Ala Tyr Cys Phe Arg Asn Val Gln Asp Asn Xaa Cys
1               5                   10                  15

Leu Arg Pro Leu Tyr Ile Asp Phe Xaa Arg Asp Leu
            20                  25
```

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:12:

```
Asp Phe Lys Arg
1
```

(2) INFORMATION FOR SEQ ID NO:13:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: unknown (ii) MOLECULE TYPE: peptide (xi) SEQUENCE DESCRIPTION: SEQ ID NO:13:

```
Asn Thr Ile Asn Pro Glu Ala Ser Ala Ser Pro Cys Cys Val Ser Gln
1               5                   10                  15
```

(2) INFORMATION FOR SEQ ID NO:14:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: unknown (ii) MOLECULE TYPE: cDNA (xi) SEQUENCE DESCRIPTION: SEQ ID NO:14:

```
Asp Ala Ala Tyr Cys Phe Arg Asn Val Gln
1               5                   10
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: unknown ( i i ) MOLECULE TYPE: cDNA ( x i ) SEQUENCE DESCRIPTION: SEQ ID NO:15:

Asp Asn Cys Cys Leu Arg Pro Leu Tyr
1               5

( 2 ) INFORMATION FOR SEQ ID NO:16:

( i ) SEQUENCE CHARACTERISTICS:
    ( A ) LENGTH: 11 amino acids
    ( B ) TYPE: amino acid
    ( C ) STRANDEDNESS: Not Relevant
    ( D ) TOPOLOGY: unknown ( i i ) MOLECULE TYPE: peptide ( x i ) SEQUENCE DESCRIPTION: SEQ ID NO:16:

Asp Thr Gln His Ser Arg Val Leu Ser Leu Tyr
1               5                   10

( 2 ) INFORMATION FOR SEQ ID NO:17:

( i ) SEQUENCE CHARACTERISTICS:
    ( A ) LENGTH: 10 amino acids
    ( B ) TYPE: amino acid
    ( C ) STRANDEDNESS: Not Relevant
    ( D ) TOPOLOGY: unknown ( i i ) MOLECULE TYPE: peptide ( x i ) SEQUENCE DESCRIPTION: SEQ ID NO:17:

Asp Asn Cys Cys Leu Arg Pro Leu Tyr Ile
1               5                   10

( 2 ) INFORMATION FOR SEQ ID NO:18:

( i ) SEQUENCE CHARACTERISTICS:
    ( A ) LENGTH: 27 amino acids
    ( B ) TYPE: amino acid
    ( C ) STRANDEDNESS: Not Relevant
    ( D ) TOPOLOGY: unknown ( i i ) MOLECULE TYPE: peptide ( x i ) SEQUENCE DESCRIPTION: SEQ ID NO:18:

Asp Thr Gln His Ser Arg Val Leu Ser Leu Tyr Asn Thr Ile Asn Pro
1               5                   10                  15

Glu Ala Ser Ala Ser Pro Cys Cys Val Ser Gln
            20              25

( 2 ) INFORMATION FOR SEQ ID NO:19:

( i ) SEQUENCE CHARACTERISTICS:
    ( A ) LENGTH: 28 amino acids
    ( B ) TYPE: amino acid
    ( C ) STRANDEDNESS: Not Relevant
    ( D ) TOPOLOGY: unknown ( i i ) MOLECULE TYPE: peptide ( x i ) SEQUENCE DESCRIPTION: SEQ ID NO:19:

Asp Leu Gly Trp Lys Trp Ile His Glu Pro Lys Gly Tyr Asn Ala Asn
1               5                   10                  15

Phe Cys Ala Gly Ala Cys Pro Tyr Leu Trp Ser Ser
            20              25

( 2 ) INFORMATION FOR SEQ ID NO:20:

( i ) SEQUENCE CHARACTERISTICS:
  ( A ) LENGTH: 31 amino acids
  ( B ) TYPE: amino acid
  ( C ) STRANDEDNESS: Not Relevant
  ( D ) TOPOLOGY: unknown ( i i ) MOLECULE TYPE: peptide ( x i ) SEQUENCE DESCRIPTION: SEQ ID NO:20:

```
Asp Leu Glu Pro Leu Thr Ile Leu Tyr Tyr Ile Gly Lys Thr Pro Lys
1               5                   10                  15

Ile Glu Gln Leu Ser Asn Met Ile Val Lys Ser Cys Lys Cys Ser
            20                  25              30
```

( 2 ) INFORMATION FOR SEQ ID NO:21:

( i ) SEQUENCE CHARACTERISTICS:
  ( A ) LENGTH: 6 amino acids
  ( B ) TYPE: amino acid
  ( C ) STRANDEDNESS: Not Relevant
  ( D ) TOPOLOGY: unknown ( i i ) MOLECULE TYPE: peptide ( x i ) SEQUENCE DESCRIPTION: SEQ ID NO:21:

```
Trp Ile His Glu Pro Lys
1               5
```

( 2 ) INFORMATION FOR SEQ ID NO:22:

( i ) SEQUENCE CHARACTERISTICS:
  ( A ) LENGTH: 5 amino acids
  ( B ) TYPE: amino acid
  ( C ) STRANDEDNESS: Not Relevant
  ( D ) TOPOLOGY: unknown ( i i ) MOLECULE TYPE: peptide ( x i ) SEQUENCE DESCRIPTION: SEQ ID NO:22:

```
Asp Leu Gly Trp Lys
1               5
```

( 2 ) INFORMATION FOR SEQ ID NO:23:

( i ) SEQUENCE CHARACTERISTICS:
  ( A ) LENGTH: 13 amino acids
  ( B ) TYPE: amino acid
  ( C ) STRANDEDNESS: Not Relevant
  ( D ) TOPOLOGY: unknown ( i i ) MOLECULE TYPE: peptide ( x i ) SEQUENCE DESCRIPTION: SEQ ID NO:23:

```
Ala Leu Asp Thr Asn Tyr Cys Phe Ser Ser Thr Glu Lys
1               5                   10
```

( 2 ) INFORMATION FOR SEQ ID NO:24:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: unknown ( i i ) MOLECULE TYPE: peptide ( x i ) SEQUENCE DESCRIPTION: SEQ ID NO:24:

```
Val Glu Gln Leu Ser Asn Met Ile Val Arg Ser Cys Lys
1               5                   10
```

( 2 ) INFORMATION FOR SEQ ID NO:25:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:25:

```
Asn  Cys  Cys  Val  Arg  Gln  Leu  Tyr  Ile  Asp  Phe  Arg  Lys
1                   5                        10
```

( 2 ) INFORMATION FOR SEQ ID NO:26:

( i ) SEQUENCE CHARACTERISTICS:
        ( A ) LENGTH: 23 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:26:

```
Gly  Tyr  His  Ala  Asn  Phe  Cys  Leu  Gly  Pro  Cys  Pro  Tyr  Ile  Trp  Ser
1                   5                        10                       15
Leu  Asp  Thr  Gln  Tyr  Ser  Lys
                20
```

( 2 ) INFORMATION FOR SEQ ID NO:27:

( i ) SEQUENCE CHARACTERISTICS:
        ( A ) LENGTH: 37 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:27:

```
Val  Leu  Ala  Leu  Tyr  Asn  Gln  His  Asn  Pro  Gly  Ala  Ser  Ala  Ala  Pro
1                   5                        10                       15
Cys  Cys  Val  Pro  Gln  Ala  Leu  Glu  Pro  Leu  Pro  Ile  Val  Tyr  Tyr  Val
                20                       25                       30
Gly  Arg  Lys  Pro  Lys
                35
```

( 2 ) INFORMATION FOR SEQ ID NO:28:

( i ) SEQUENCE CHARACTERISTICS:
        ( A ) LENGTH: 35 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:28:

```
Val  Leu  Ala  Leu  Tyr  Asn  Gln  His  Asn  Pro  Gly  Ala  Ser  Ala  Ala  Pro
1                   5                        10                       15
Cys  Cys  Val  Pro  Gln  Ala  Leu  Glu  Pro  Leu  Pro  Ile  Val  Tyr  Tyr  Val
                20                       25                       30
Gly  Arg  Lys
           35
```

( 2 ) INFORMATION FOR SEQ ID NO:29:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:29:

```
Glu  Asn  Cys  Cys  Val  Arg  Pro  Leu  Tyr
1                   5
```

( 2 ) INFORMATION FOR SEQ ID NO:30:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:30:

```
Asp  Thr  Asn  Tyr  Cys  Phe  Arg  Asn  Leu  Glu
1                   5                        10
```

( 2 ) INFORMATION FOR SEQ ID NO:31:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:31:

```
Asp  Thr  Thr  His  Ser  Thr  Val  Leu  Gly  Leu  Tyr
1                   5                        10
```

( 2 ) INFORMATION FOR SEQ ID NO:32:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:32:

```
Asp  Thr  Asn  Tyr  Cys  Phe  Arg  Asn  Leu
1                   5
```

( 2 ) INFORMATION FOR SEQ ID NO:33:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: unknown ( i i ) MOLECULE TYPE: protein ( x i ) SEQUENCE DESCRIPTION: SEQ ID NO:33:

```
Asp  Thr  Thr  His  Ser  Thr  Val  Leu  Gly  Leu  Tyr  Asn  Thr
1                   5                        10
```

( 2 ) INFORMATION FOR SEQ ID NO:34:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:34:

```
Asp Leu Glu Pro Leu Thr Ile Leu Tyr Tyr Val Gly Arg
1               5                   10
```

( 2 ) INFORMATION FOR SEQ ID NO:35:

( i ) SEQUENCE CHARACTERISTICS:
        ( A ) LENGTH: 27 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:35:

```
Asp Thr Thr His Ser Thr Val Leu Gly Leu Tyr Asn Thr Leu Asn Pro
1               5                   10                  15
Glu Ala Ser Ala Ser Pro Cys Cys Val Pro Gln
                20                  25
```

( 2 ) INFORMATION FOR SEQ ID NO:36:

( i ) SEQUENCE CHARACTERISTICS:
        ( A ) LENGTH: 20 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:36:

```
Asp Thr Asn Tyr Cys Phe Arg Asn Leu Glu Glu Asn Cys Cys Val Arg
1               5                   10                  15
Pro Leu Tyr Ile
                20
```

( 2 ) INFORMATION FOR SEQ ID NO:37:

( i ) SEQUENCE CHARACTERISTICS:
        ( A ) LENGTH: 28 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:37:

```
Asp Leu Gly Trp Lys Trp Val His Glu Pro Lys Gly Tyr Tyr Ala Asn
1               5                   10                  15
Phe Cys Ser Gly Pro Cys Pro Tyr Leu Arg Ser Ala
                20                  25
```

( 2 ) INFORMATION FOR SEQ ID NO:38:

( i ) SEQUENCE CHARACTERISTICS:
        ( A ) LENGTH: 31 amino acids
        ( B ) TYPE: amino acid
        ( C ) STRANDEDNESS: Not Relevant (D) TOPOLOGY: unknown (ii) MOLECULE TYPE: peptide (xi) SEQUENCE DESCRIPTION: SEQ ID NO:38:

```
Asp Leu Glu Pro Leu Thr Ile Leu Tyr Tyr Val Gly Arg Thr Pro Lys
 1               5                  10                  15
Val Glu Gln Leu Ser Asn Met Val Val Lys Ser Cys Lys Cys Ser
                20                  25                  30
```

(2) INFORMATION FOR SEQ ID NO:39:

(i) SEQUENCE CHARACTERISTICS:
      (A) LENGTH: 58 amino acids
      (B) TYPE: amino acid
      (C) STRANDEDNESS: Not Relevant
      (D) TOPOLOGY: unknown (ii) MOLECULE TYPE: peptide (xi) SEQUENCE DESCRIPTION: SEQ ID NO:39:

```
Asp Thr Thr His Ser Thr Val Leu Gly Leu Tyr Asn Thr Leu Asn Pro
 1               5                  10                  15
Glu Ala Ser Ala Ser Pro Cys Cys Val Pro Gln Asp Leu Glu Pro Leu
                20                  25                  30
Thr Ile Leu Tyr Tyr Val Gly Arg Thr Pro Lys Val Glu Gln Leu Ser
                35                  40                  45
Asn Met Val Val Lys Ser Cys Lys Cys Ser
                50                  55
```

(2) INFORMATION FOR SEQ ID NO:40:

(i) SEQUENCE CHARACTERISTICS:
      (A) LENGTH: 29 amino acids
      (B) TYPE: amino acid
      (C) STRANDEDNESS: Not Relevant
      (D) TOPOLOGY: unknown (ii) MOLECULE TYPE: peptide (xi) SEQUENCE DESCRIPTION: SEQ ID NO:40:

```
Ala Leu Asp Ala Ala Tyr Xaa Phe Arg Asn Val Gln Asp Asn Xaa Xaa
 1               5                  10                  15
Leu Arg Pro Leu Tyr Ile Asp Phe Lys Arg Asp Leu Gly
                20                  25
```

(2) INFORMATION FOR SEQ ID NO:41:

(i) SEQUENCE CHARACTERISTICS:
      (A) LENGTH: 112 amino acids
      (B) TYPE: amino acid
      (D) TOPOLOGY: linear (ii) MOLECULE TYPE: protein (xi) SEQUENCE DESCRIPTION: SEQ ID NO:41:

```
Ala Leu Asp Thr Asn Tyr Cys Phe Ser Ser Thr Glu Lys Asn Cys Cys
 1               5                  10                  15
Val Arg Gln Leu Tyr Ile Asp Phe Arg Lys Asp Leu Gly Trp Lys Trp
                20                  25                  30
Ile His Glu Pro Lys Gly Tyr His Ala Asn Phe Cys Leu Gly Pro Cys
                35                  40                  45
Pro Tyr Ile Trp Ser Leu Asp Thr Gln Tyr Ser Lys Val Leu Ala Leu
                50                  55                  60
```

-continued

| | | | | | | | | | | | | | | |
|---|---|---|---|---|---|---|---|---|---|---|---|---|---|---|
| Tyr | Asn | Gln | His | Asn | Pro | Gly | Ala | Ser | Ala | Ala | Pro | Cys | Cys | Val | Pro |
| 65 | | | | | 70 | | | | 75 | | | | | | 80 |
| Gln | Ala | Leu | Glu | Pro | Leu | Pro | Ile | Val | Tyr | Tyr | Val | Gly | Arg | Lys | Pro |
| | | | | 85 | | | | | 90 | | | | | 95 | |
| Lys | Val | Glu | Gln | Leu | Ser | Asn | Met | Ile | Val | Arg | Ser | Cys | Lys | Cys | Ser |
| | | | 100 | | | | | 105 | | | | | 110 | | |

( 2 ) INFORMATION FOR SEQ ID NO:42:

( i ) SEQUENCE CHARACTERISTICS:
( A ) LENGTH: 112 amino acids
( B ) TYPE: amino acid
( D ) TOPOLOGY: linear ( i i ) MOLECULE TYPE: protein ( x i ) SEQUENCE DESCRIPTION: SEQ ID NO:42:

| Ala | Leu | Asp | Ala | Ala | Tyr | Cys | Phe | Arg | Asn | Val | Gln | Asp | Asn | Cys | Cys |
|---|---|---|---|---|---|---|---|---|---|---|---|---|---|---|---|
| 1 | | | | 5 | | | | | 10 | | | | | 15 | |
| Leu | Arg | Pro | Leu | Tyr | Ile | Asp | Phe | Lys | Arg | Asp | Leu | Gly | Trp | Lys | Trp |
| | | | 20 | | | | | 25 | | | | | 30 | | |
| Ile | His | Glu | Pro | Lys | Gly | Tyr | Asn | Ala | Asn | Phe | Cys | Ala | Gly | Ala | Cys |
| | | 35 | | | | | 40 | | | | | 45 | | | |
| Pro | Tyr | Leu | Trp | Ser | Ser | Asp | Thr | Gln | His | Ser | Arg | Val | Leu | Ser | Leu |
| | 50 | | | | | 55 | | | | | 60 | | | | |
| Tyr | Asn | Thr | Ile | Asn | Pro | Glu | Ala | Ser | Ala | Ser | Pro | Cys | Cys | Val | Ser |
| 65 | | | | | 70 | | | | 75 | | | | | | 80 |
| Gln | Asp | Leu | Glu | Pro | Leu | Thr | Ile | Leu | Tyr | Tyr | Ile | Gly | Lys | Thr | Pro |
| | | | | 85 | | | | | 90 | | | | | 95 | |
| Lys | Ile | Glu | Gln | Leu | Ser | Asn | Met | Ile | Val | Lys | Ser | Cys | Lys | Cys | Ser |
| | | | 100 | | | | | 105 | | | | | 110 | | |

( 2 ) INFORMATION FOR SEQ ID NO:43:

( i ) SEQUENCE CHARACTERISTICS:
( A ) LENGTH: 112 amino acids
( B ) TYPE: amino acid
( D ) TOPOLOGY: linear ( i i ) MOLECULE TYPE: protein ( x i ) SEQUENCE DESCRIPTION: SEQ ID NO:43:

| Ala | Leu | Asp | Thr | Asn | Tyr | Cys | Phe | Arg | Asn | Leu | Glu | Glu | Asn | Cys | Cys |
|---|---|---|---|---|---|---|---|---|---|---|---|---|---|---|---|
| 1 | | | | 5 | | | | | 10 | | | | | 15 | |
| Val | Arg | Pro | Leu | Tyr | Ile | Asp | Phe | Arg | Gln | Asp | Leu | Gly | Trp | Lys | Trp |
| | | | 20 | | | | | 25 | | | | | 30 | | |
| Val | His | Glu | Pro | Lys | Gly | Tyr | Tyr | Ala | Asn | Phe | Cys | Ser | Gly | Pro | Cys |
| | | 35 | | | | | 40 | | | | | 45 | | | |
| Pro | Tyr | Leu | Arg | Ser | Ala | Asp | Thr | Thr | His | Ser | Thr | Val | Leu | Gly | Leu |
| | 50 | | | | | 55 | | | | | 60 | | | | |
| Tyr | Asn | Thr | Leu | Asn | Pro | Glu | Ala | Ser | Ala | Ser | Pro | Cys | Cys | Val | Pro |
| 65 | | | | | 70 | | | | 75 | | | | | | 80 |
| Gln | Asp | Leu | Glu | Pro | Leu | Thr | Ile | Leu | Tyr | Tyr | Val | Gly | Arg | Thr | Pro |
| | | | | 85 | | | | | 90 | | | | | 95 | |
| Lys | Val | Glu | Gln | Leu | Ser | Asn | Met | Val | Val | Lys | Ser | Cys | Lys | Cys | Ser |
| | | | 100 | | | | | 105 | | | | | 110 | | |

PROCESS FOR REFOLDING RECOMBINANTLY PRODUCED TGF-β-LIKE PROTEINS

This application is a continuation of application Ser. No. 08/201,703, filed Feb. 25, 1994, now abandoned which is a continuation of application Ser. No. 07/960,309, filed Oct. 13, 1992, now abandoned, which is a continuation of application Ser. No. 07/621,502, filed Dec. 3, 1990, now abandoned.

The present invention relates to a process for the preparation of biologically active, dimeric, TGF-β (Transforming Growth Factor type β), to novel TGF-βs, and pharmaceutical compositions comprising it. TGF-β produced according to the invention can be used for the promotion and acceleration of wound healing and bone and tissue repair, the treatment of cancer, as a bone marrow protective agent, mediator of cardioprotection, anti-inflammatory or immunosuppressive agent or as a growth regulator in mammalian cell cultures.

BACKGROUND OF THE INVENTNION

Two growth modulating proteins have originally been characterized by their ability to reversibly induce phenotypic transformation of mammalian cells in vitro and have therefore been designated as Transforming Growth Factors type α and type β (Anzano, M. A. et al. (1983) PNAS 80, 6264–6268). Despite their common nomenclature TGF-α and TGF-β have shown to be both structurally as well as functionally entirely distinct proteins each acting through its own unique receptor system. TGF-α which competes with epidermal growth factor (EGF) for binding to the same cell surface receptor (Todaro, G. J. et al. (1980) PNAS 77, 5258–5262) and which shares sequence homologies and similar activity with EGF (Marquardt, H. et al. (1984) Science 223, 1079–1082) is synthesized as a transmembraneous precursor of 159 amino acids and is proteolytically processed into a peptide of 50 amino acid residues (Derynck, R. et al. (1984) Cell 38, 287–297). As a potent mitogen for mesenchymal cells, TGF-α is produced and released by numerous transformed cell lines and human cancers, but is also expressed in activated macrophages and in other normal tissues, thus making its role in neoplasia still unclear.

TGF-β was originally purified to homogeneity from human platelets (Assoian, R. K. et al. (1983) J. Biol. Chem. 258, 7155–7160), human placenta (Frolik, C. A. et al. (1983) PNAS 80, 3676–3680) and bovine kidney (Roberts, A. B. et al. (1983) Biochemistry 22, 5692–5698) and identified as a homodimeric protein with a molecular mass of 25,000 D. First characterized by its ability to act synergistically with EGF or TGF-α to induce anchorage-independent growth of untransformed NRK cells, recently, TGF-β has been shown to exhibit numerous regulatory effects on a wide variety of both normal and neoplastic cells indicating the importance of this protein as a multifunctional regulator of cellular activity. TGF-β may either stimulate mitogenesis, cell proliferation and growth, or may effectively inhibit said processes, or may exhibit other actions like e.g. control of adipogenesis, myogenesis, chondrogenesis, osteogenesis und immune cell function, stimulation of chemotaxis, or induction or inhibition of differentiation depending upon the cell or tissue type, and the presence or absence of other growth factors. Many of the actions of TGF-β are related to the response of cells or tissues to stress or injury, and to the repair of resultant damage. After inflammation, TGF-β plays the major role in the formation of granulation tissue, increases the expression of genes associated with extracellular matrix formation such as fibronectin, collagen and several protease inhibitors and stimulates collagen-matrix contraction by fibroblasts, suggesting its possible role in connective tissue contraction (Roberts, A. and Sporn, M. B. (1988) Adv. Cancer Res. 51, 107–145; Sporn, M. B. and Roberts, A. (1989) J. Amer. Med. Assoc. 262, 938–941).

Until now, three distinct types of TGF-βs designated as TGF-β1, TGF-β2 and TGF-β3 which are functionally closely related and share a high degree of receptor cross-reactivity have been cloned and characterized by sequence analysis. All TGF-βs are synthesized as 390 to 412 amino acid precursors that undergo proteolytic cleavage to produce the monomeric forms, which consist of the C-terminal 112 amino acids. In their mature, biologically active forms, TGF-βs are acid- and heat-stable disulfide-linked homodimers of two polypeptide chains of 112 amino acids each. The complete amino acid sequences of human (Derynck, R. et al. (1985) Nature 316, 701–705), murine (Derynck, R. et al. (1986) J. Biol. Chem. 261, 4377–4379) and simian TGF-β1 (Sharples, K. et al. (1987) DNA 6, 239–244) show remarkable sequence conservation, differing only in a single amino acid residue. Comparison of the amino acid sequence of human TGF-β1, human TGF-β2 (de Martin, R. et al. (1987) EMBO J. 6, 3673–3677; Marquardt, H. et al. (1987) J. Biol. Chem. 262, 12127–12131) and human TGF-β3 (Ten Dijke, P. et al. (1988) PNAS 85, 4715–4719) has demonstrated that the three proteins exhibit in their mature forms about 70–80% sequence identity. A heterodimeric TGF-β1.2 has been isolated from porcine platelets and consists of one subunit of TGF-β1 disulfide-linked to one subunit of TGF-β2 (Cheifetz, S. et al. (1987) Cell 48, 409–415).

Recently, attempts have been undertaken aiming to produce TGF-βs by means of recombinant techniques rather than isolating these factors from natural sources (e.g. platelets) in order to obtain sufficient amounts for testing in various therapeutic modalities. However, it has proven to be extremely difficult to synthesize recombinant TGF-β while retaining its biological activity. As can be seen from the sequences depicted in the sequence listing under SEQ ID No. 1, 2, and 3 and 41, 42 and 43, the 112 amino acids containing mature forms of TGF-β1, TGF-β2 and TGF-β3 contain 9 cysteine residues each, at least some of which are involved in intrachain and interchain disulfide bond formation which results in the complex tertiary structure of the biologically active, dimeric molecules. Heterologous expression of TGF-β may lead to a product which, although having the correct primary structure, fails to fold properly to produce the correct secondary or tertiary structures and which, therefore, lacks the biological activity. To date, the secondary and tertiary structures of TGF-βs are unknown.

Taking the complexity of the native TGF-β molecules into account, it has generally been considered expedient to express the respective TGF-β genes in cells derived from higher organisms. The expression of simian and human TGF-β1 in Chinese hamster ovary (CHO) cells under the control of the SV40 promoter is described in European Patent Applications 293,785 and 200,341, respectively. Recombinant TGF-β2 could be expressed in the same cell line as disclosed in European Patent Application 268,561 and in German Offenlegungsschrift 38 33897. Eukaryotic expression of a fusion protein of TGF-β3 (with TGF-β1) is disclosed in European Patent Application 267,463.

Although expression of recombinant TGF-βs can be achieved in eukaryotic systems, the yields of biologically active, correctly folded material obtained are still far from being satisfactory. On the other hand, it seemed unlikely that biologically active TGF-β could be obtained when the respective gene was expressed in a microbial host, since in e.g. bacteria the intracellular conditions are not conducive to refolding, disulfide bond formation and disulfide-stabilized dimerization which is apparently essential for activity. Thus, only very little biologically active TGF-β2 could be obtained after expression of the respective gene in *E. coli* under the control of the lambda promoter as described in European Patent Application 268,561. This lack of activity is considered to be due to the fact, that the biologically active, dimeric form of TGF-β2 fails to form spontaneously from the monomeric primary translation product when exposed to the reducing environment inside the bacterial cells. Another report describes the expression of TGF-β cDNA in *E. coli* under the control of the trp promoter yielding a radioactively labelled protein band with an apparent molecular weight of 13,000 D in an autoradiogram of a SDS polyacrylamide gel, but no activity was measured (Urushizaki, Y. et al. (1987) Tumor Res. 22, 41–55).

When recombinant proteins are produced at high levels in bacterial (such as *E. coli*) expression systems, they often appear in the form of highly insoluble intracellular precipitates referred to as inclusion bodies or refractile bodies (Brems, D. N. et al. (1985) Biochemistry 24, 7662) which can be recognized as bright spots visible within the enclosure of the cells under a phase contrast microscope at magnifications down to 1000 fold. These inclusion bodies, which can readily be separated from the soluble bacterial proteins, contain the recombinant protein in a mostly denatured and reduced form which does not exhibit the functional activity of its natural counterpart and which therefore is useless as a commercial product.

It is therefore generally agreed, that the recombinant refractile protein has to be solubilized under conditions which are suitable in maintaining it in its denatured form and subsequently has to be refolded in order to undergo the transition from the denatured unfolded form to the proper, functionally active three-dimensional structure, the conformation of which is stabilized by relatively weak interatomic forces such as hydrogen bonding, hydrophobic interactions and charge interactions. In the case of cysteine containing proteins this process may also involve formation of disulphide bonds. When the formation of disulfide bonds is chemically promoted, the formation of incorrect intramolecular and, in the case of dimeric or multimeric proteins, intermolecular bridges should be prevented or at least minimized, since the formation of undesired, incorrectly folded isomers may yield non-homogenous material, thus complicating the further purification of the protein having the desired structure, or may generate a protein with reduced activity.

A number of publications have appeared which report refolding attempts for individual proteins produced in bacterial hosts, or which are otherwise in a denatured or non-native form. Formation of a dimeric, biologically active human colony stimulating factor-1 (CSF-1) after expression in *E. coli* is described in PCT Application No. 88/8003 and by Halenbeck, R. et al. (1989) Biotechnology 7, 710–715. The procedures described involve the steps of initial solubilization of CSF-1 monomers isolated from inclusion bodies under reducing conditions in a chaotropic environment comprising urea or guanidine hydrochloride, refolding which is achieved by stepwise dilution of the chaotropic agents, and final oxidation of the refolded molecules in the presence of air or a redox-system. In PCT Application No. 88/8849 a process for recovering recombinant interleukin-2 (IL-2) is disclosed, characterized in that IL-2 isolated from refractile bodies is denatured under reducing conditions with 6M guanidine hydrochloride, the soluble IL-2 is oxidized by a controlled oxidization in the presence of $Cu^{2+}$ ions, and the oxidized IL-2 is refolded by reducing the concentration of the denaturant in the solution. Interleukin-2 and interferon-μ (IFN-β) have been refolded using SDS for solubilization and $Cu^{2+}$ ions as oxidation promoters of the fully reduced proteins (U.S. Pat. No. 4,572,798). The process for isolating recombinant refractile proteins as described in U.S. Pat. No. 4,620,948 involves strong denaturing agents to solubilize the proteins, reducing conditions to facilitate correct folding and denaturant replacement in the presence of air or other oxidizing agents to reform the disulfide bonds. The proteins to which said process can be applied include urokinase, human, bovine and porcine growth hormone, interferon, tissue-type plasminogen activator, FMD coat protein, prorennin and the src protein. A method for renaturing unfolded proteins including cytochrome c, ovalbumin and trypsin inhibitor by reversibly binding the denatured protein to a solid matrix and stepwise renaturing it by diluting the denaturant is disclosed in PCT Application No. 86/5809. A modified monomeric form of human platelet-derived growth factor (PDGF) expressed in *E. coli* is S-sulfonated during purification in order to protect thiol moieties and is dimerized in the presence of oxidizing agents to yield the active protein (Hoppe, J. et al. (1989) Biochemistry 28, 2956).

The foregoing references are merely representatives of a huge amount of literature dealing with the refolding of non-native proteins derived from different sources. The man skilled in the art on the other hand knows that the success of refolding experiments cannot be predicted. Unsuccessful experiments are usually not reported. There is no certainty that anyone of the reported refolding conditions would work at all with a given denatured protein such as TGF-β. Considering the fact, that TGF-β is a dimeric protein containing 9 cysteine residues per chain and a number of intramolecular as well as intermolecular disulfide bonds, which are required for activity, it is a particularly difficult challenge to produce biologically active TGF-β from its monomeric, denatured or otherwise non-native form. Nowhere in the literature is a specific process described for the preparation of biologically active dimeric TGF-β from its non-native form.

OBJECT OF THE INVENTION

It is the object of the present invention to provide a process for the production of biologically active, dimeric TGF-β-like protein from its denatured or otherwise non-native form. This object is achieved by the unexpected finding that considerable amounts of the desired dimeric product can be obtained when the monomeric form of said protein is subjected to refolding conditions. Surprisingly, the production of the active dimer is achieved under various conditions in a one step procedure which is superior over the multi-step procedures described in the prior art for the refolding of other proteins.

DETAILED DESCRITPION OF THE INVENTION

The present invention relates to a process for the production of a dimeric, biologically active Transforming Growth Factor type β (TGF-β)-like protein, comprising subjecting the denatured, monomeric form of said TGF-β-like protein to refolding conditions.

The term "TGF-β-like protein" is intended to embrace TGF-β1, TGF-β2 and TGF-β3 of mammalian such as human or animal origin, e.g. simian, murine, porcine, equine or bovine, as well as heterodimeric TGF-βs consisting of two different subunits of 112 amino acids each. Further included within the definition are growth-regulating proteins of the TGF-β superfamily sharing a sequence homology of at least about 25% with TGF-β1, TGF-β2 or TGF-β3, such as a T cell suppressor factor from human glioblastoma cells (G-TsF; Wrann, M. et al. (1987) EMBO J. 6, 1633–1636), a growth inhibitor isolated from conditioned medium of BSC-1 monkey kidney cells (polyergin; Holley, R. W. et al. (1980) PNAS 77, 5989–5992; Ristow, H. J. (1986) PNAS 83, 5531–5533) a cartilage-inducing peptide isolated from bovine bone (CIF-B; Seyedin, S. M. et al. (1987) J. Biol. Chem. 262, 1946–1949), TGF-β4 from chicken embryo chondrocytes (Jakowlew, S. B. et al. (1988) Molecular Endocrinology 2, 1186–1195) and TGF-β5 from Xenopus-Laevis (Kondaiah, P. et al. (1990) J. Biol. Chem. 265, 1089–1093), as well as fragments and mutants of the above mentioned proteins retaining the biological activity. Further included within the definition of "TGF-β-like protein" are two forms of inhibin and three forms of activin (gonadal proteins that regulate pituitary secretion of follicle stimulating hormone), Mullerian inhibiting substance (MIS, which inhibits the development of the Mullerian duct in mammalian male embryos), bone morphogenic proteins (BMP, a group of polypeptides involved in the induction of cartilage and bone formation), the transcript from the decapentaplegic gene complex of Drosophila (dpp, which acts to control morphogenesis in the fly embryo), Vg-1 (the product of the Xenopus transcript which is present in the vegetal pole of oocytes), and Vgr-1, a related mammalian gene (Mason, A. et al. (1986) Biochem. Biophys. Res. Commun. 135, 957–964; Cate, R. et al. (1986) Cell 45, 685–698; Wozney, J. M. et al. (1988) Science 242, 1528–1534; Padgett, R. et al. (1986) Nature 325, 81–84; Weeks, D. L. and Melton, D. A. (1987) Cell 51, 861–868; Lyons, K. et al. (1989) PNAS 86, 4554–4558).

Preferred TGF-β-like proteins are human TGF-β1 (Derynck, R. et al. (1985) Nature 316, 701–705), human TGF-β2 (Marquardt, H. et al. (1987) J. Biol. Chem. 262, 12127–12131) and human TGF-β3 (Ten Dijke, P. et al. (1988) PNAS 85, 4715–4719) with the amino acid sequences depicted in the sequence listing under SEQ ID No. 1, 2 and 3, respectively.

Biologically active TGF-β-like proteins are originally defined as being capable of inducing anchorage-independent growth of untransformed cell lines (Tucker, R. F. et al. (1983) Cancer Research 43, 1581–1586) or inhibiting growth of neoplastic target cells (Roberts, A. B. et al. (1985) PNAS 82, 119–123). "Biological activity" for the purpose herein is defined as either (a) the cell migration promoting activity on normal Balb/c 3T3 fibroblasts, which can be measured by counting the number of cells that migrate into a "wounded" mono-layer culture of said cells, in the presence of a serum-free medium containing the TGF-β-like protein, as compared to the number of cells that migrate in the absence of the TGF-β-like protein, or (b) the growth promoting activity on normal Balb/c 3T3 fibroblasts determined by the stimulatory effect of the TGF-β-like protein on cellular DNA synthesis and cell division, (c) the growth inhibition of A375 melanoma cells determined by a colorimetrical assay which reflects the number of cells treated with the TGF-β-like protein for a given culture period as compared to the number of non-treated cells, (d) the accelerated healing of partial-thickness burn wounds, by a process of re-epithelialization, in old mice following multiple topical applications of the TGF-β-like protein as compared to untreated control wounds, (e) the accelerated healing of full-thickness incisional wounds, as determined by tensile strength measurements and the histological analyses of biopsies, in adult rats following single topical applications of the TGF-β-like protein as compared to untreated control wounds, or (f) the increase in formation of fibrous granulation tissue, together with a marked increase in vascularity of the said tissue, both in and around porous wound-chamber implants in adult rats following multiple local injections of the TGF-β-like protein into the chamber as compared to untreated control chambers.

The monomeric form of the TGF-β-like protein can be produced by means of recombinant DNA technology or synthetically by methods well known in the art. The dimeric form is the mature, biologically active molecule consisting of two disulfide-linked polypeptide chains.

The monomer is subjected to refolding conditions which allow the recovery of the biologically active dimer. This process does not involve any change in the primary structure (i.e. the amino acid sequence) of the monomer, but relates to the formation of the three-dimensional conformation of the dimeric product which is associated with the biological activity. This process includes the formation of disulfide bonds and the association of monomers into dimeric structures.

Before being subjected to refolding conditions, the monomeric TGF-β-like protein has to be present in a denatured (i.e. unfolded) form. Capable of effectively denaturing proteins are so-called chaotropic agents well known in the art, which, in aqueous solution and in suitable concentrations change the spatial configuration of the respective protein through alterations at the surface thereof, either through altering the state of hydration, the solvent environment, or the solvent-surface interaction. Examples of such chaotropic agents or denaturants include urea, guanidine hydrochloride, sodium thiocyanate at concentrations in the range of about 4 to about 9M, and detergents such as SDS, which are supplied in concentrations in the order of 0.01 to 2 percent. Also, acidification of the aqueous solution containing the TGF-β-like protein to a pH of about 2 to about 4 as well as basic conditions of e.g. pH 10 and above and elevated temperatures will result in denaturation of the monomer.

The term "refolding conditions" refers to buffer conditions wherein the denatured monomer is permitted to assume a conformation associated with the biological activity. Conventional buffer systems such as Tris, phosphate or citrate buffers can be used at a pH of about 6 to about 10. Under refolding conditions intra- and interchain disulfide bond formation is promoted. Such conditions include the presence of a solubitizing agent and a redox system which permits the continuous oxidation and reduction of the thiol/disulfide pairs. The buffer system may additionally contain suitable salts.

Suitable solubilizing agents are detergents, preferably mild detergents, organic, water-miscible solvents, or phospholipids or a mixture of two or more such agents.

Detergents are surface active compounds, such as SDS, Triton or Tween, used in a concentration permitting folding of the TGF-β-like protein. Preferred are mild detergents which permit folding of the monomeric TGF-β-like protein into the spatial conformation which after dimerization is associated with the biological activity, while retaining said monomer in a soluble form. Mild detergents, which solubilize TGF-β-like proteins without inactivating them can be non-ionic (e.g. digitonin), cationic (e.g. N-[2,3-(Dioleyloxy)-propyl]-N,N,N-trimethylammonium; Düzgünes, N. et al.

(1989) Biochemistry 28, 9179–9184) or anionic (e.g. sodium cholate, sodium deoxycholate) or zwitterionic ones (e.g. sulfobetaines (Zwittergent), 3-(3-chlolamidopropyl) dimethylammonio- 1-propane-sulfonate (Chaps), 3-(3-chlolamidopropyl)dimethylammonio-2-hydroxy-1-propanesulfonate (Chapso)). They are present in the refolding buffer at a concentration of about 1 to 100 mM, especially in the range of 30 to 60 mM. Preferred detergents are the zwitterionic detergents 3-(3-chlolamidopropyl) dimethylammonio-1-propanesulfonate and 3-(3-chlolamidopropyl)dimethylammonio-2-hydroxy-1-propanesulfonate. Most preferred is 3-(3-chlolamidopropyl) dimethylammonio-1-propanesulfonate.

Organic, water-miscible solvents can replace the detergent in the refolding buffer. Such solvents are, for example, acetonitrile, lower alkanols, especially $C_2$–$C_4$ alkanols such as ethanol or isopropanol, or lower alkandiols, especially $C_2$–$C_4$ alkandiols such as ethylene-glycol, at a concentration range of 10 to 50 percent per volume.

Alternatively, phospholipids can replace the detergent or the organic, water-miscible solvent in the refolding buffer. Such phospholipids are, for example, phosphatidylethanolamine, phosphatidylcholine, phosphatidylserine and phosphatidylinositole at a concentration range of 0.1 to 5 mg/ml as well as synthetic phospholipid derivatives or variants such as dihexanoylphosphatidylcholine or diheptanoylphosphatidylcholine in the same concentration range.

Suitable redox systems which encourage the formation of disulfides are e.g. low molecular weight sulfhydryl/disulfide reagent combinations such as glutathione in its oxidized and reduced form, dithiothreitol in its oxidized and reduced form, β-mercaptoethanol or β-mercaptomethanol in its oxidized and reduced form, cystine and its reduced form, and cystamine and its reduced form at a concentration of about 1 to 100 mM, especially of about 1 to 10 mM, wherein the molar ratio of the oxidized and the reduced form is between 100:1 and 1:100, especially between 6:1 and 1:6.

The preferred sulfhydryl/disulfide redox system is glutathione in its oxidized and reduced form.

Alternatively, thioredoxin or disulfideisomerase at a concentration range of about 10 to 1000 µg/ml, especially of about 50 to 200 µg/ml can be used instead of the low molecular weight sulfhydryl/disulfide reagent combinations.

Salts which can be used in the refolding buffer include salts of $Na^+$, $Li^+$, $K^+$, $NH_4^+$, $Mg^{2+}$, $Ca^{2+}$, or $Mn^{2+}$ with $Cl^-$, $F^-$, $Br^-$, $I^-$, $HCO_3^-$, $SO_4^{2-}$, phosphate, acetate, cyanate or rhodanid, or other alkali metal- or alkaline earthmetal— halogen or pseudohalogen compounds at a concentration of up to 3M. Preferred is NaCl at a concentration of 1 to 2M.

The invention particularly relates to a process for the production of a dimeric, biologically active Transforming Growth Factor type β-like protein, comprising subjecting the denatured, monomeric form of said TGF-β-like protein to buffer conditions comprising a low molecular weight sulfhydryl/disulfide redox system in the presence of a solubilizing agent at a pH of about 6 to about 10 and a temperature of about 0° C. to about 37° C. Preferably, the pH is about 8.0 and the temperature is about 4° C.

In a preferred embodiment the sulfhydryl/disulfide redox system is glutathione in its oxidized and reduced form at a concentration of about 1 to 10 mM, wherein the molar ratio of the oxidized and the reduced form is 1:1 to 1:2, and the weak detergent is 3-(3-chlolamidopropyl) dimethylammonio-1-propanesulfonate at a concentration of about 30 mM to about 60 mM.

Particularly, the production of a dimeric, biologically active TGF-β-like protein is performed in a one step procedure, wherein the monomer of said protein is dissolved in the refolding buffer and the reaction mixture is incubated for 2 to 400 hours at 4° C. while folding and dimerization continuously take place. The protein concentration during the refolding reaction is of considerable importance since when being too high, the monomers might undergo substantial aggregation leading to the formation of undesired higher-order oligomers. Final yields of dimeric product are increased, if the protein concentration is less than about 2 mg/ml, a concentration range of 0.01 to 0.5 mg/ml is preferred.

Optionally, to further promote disulfide formation, an effective amount of an oxidation promoting agent containing $Cu^{2+}$ ions (such as $CuCl_2$, $Cu(NO_3)_2$ or o-phenanthroline/ $Cu^{2+}$ complexes) or $Fe^{3+}$ ions (such as $FeCl_3$ or $Fe_2(SO_4)_3$) might be added to the refolding buffer. An effective amount is the amount which at minimum will be necessary to conduct the oxidation of sulfhydryl groups within a convenient time period and which is approximately equivalent to the concentration of free sulfhydryl groups in the TGF-β-like protein which are destined to be involved in forming the desired disulfide bonds. Preferable amounts range between 0.01 to 100 µM.

Furthermore, $O_2$ or air may optionally be bubbled through the refolding buffer either in the presence or absence of oxidation promoting agents. Oxidation may also be performed using $I_2$ (Kamber, B. et al., 1980. Helv. 63, 899–915) or Benzochinon derivatives (Kamber, B. PCT appl. WO 89/01484).

Sulfonation of proteins can be used to cleave disulfide bonds and to block the resulting thiol groups. Monomeric TGF-β-like proteins can optionally be S-sulfonated and thereby be prevented to become oxidized before being exposed to the refolding conditions. S-sulfonation is performed using sodium sulfite in the presence of a reducing agent such as cysteine, resulting in the reversible protection of thiol residues as S-sulfonates. Under refolding conditions, the protection groups are removed by the excess of the sulfhydryl/disulfide redox system and dimerization occurs spontaneously.

The invention relates further to a process for the production of a dimeric, biologically active TGF-β-like protein, in which the monomeric form of said TGF-β-like protein is produced by the steps of:

(a) culturing a microbial host comprising a nucleotide sequence encoding the TGF-β-like protein linked in the proper reading frame to an expression control sequence such that said protein is expressed, (b) recovering the TGF-β-like protein in a denatured, monomeric, soluble form, Suitable microbial hosts are yeast strains as *Saccharomyces cerevisiae* or bacteria such as *Escherichia coli* or *Bacillus subtilis*.

Microbial hosts comprising a nucleotide sequence encoding the TGF-β-like protein linked in the proper reading frame to an expression control sequence can be prepared by recombinant DNA techniques which are well known in the art and which comprise the steps of preparing a hybrid vector comprising a DNA sequence encoding the TGF-β-like protein under the expression control of a suitable expression control sequence, transforming said microbial host with said hybrid vector, and selecting transformed microbial host cells from untransformed host cells.

The nucleotide sequence coding for TGF-β-like proteins such as mature human TGF-β1, TGF-β2 or TGF-β3 are known (Derynck, R. et al. (1985) Nature 316, 701–705; Marquardt, H. et al. (1987) J. Biol. Chem. 262, 12127–12131; Ten Dijke, P. et al. (1988) PNAS 85, 4715–4719) and can e.g. be chemically synthesized by methods known in the art. Alternatively, cDNAs encoding TGF-β-like proteins can be prepared after isolation of the respective mRNA from TGF-β-like proteins producing mammalian cells. Expression control sequences are promoter sequences which ensure the effective expression of the TGF-β-like proteins.

The selection of a suitable vector is determined by the microbial host cell provided for the transformation.

Examples of vectors that are suitable for the expression of the TGF-β-like protein in an *E. coli* strain are bacteriophages, for example derivatives of the bacteriophage λ, or plasmids, such as the plasmid pBR322 and its derivative pPLMu. Suitable vectors contain a complete replicon and a marker gene, which renders possible the selection and identification of the microorganisms transformed by the expression plasmids by means of a phenotype feature. Suitable marker genes impart to the microorganism, for example, resistance to heavy metals, antibiotics such as ampicillin or tetracyclin, and the like.

Several promoters can be used for regulating the expression of TGF-β-like proteins in *E. coli*. Especially promoters of strongly expressed genes are used. Suitable promoters are the *E. coli* lac, tac, trp and lpp promoters, furthermore the phage λN or the phage λpL promoter, and others.

Vectors suitable for replication and expression in *S. cerevisiae* contain a yeast-replication origin and a selective genetic marker for yeast. Hybrid vectors that contain a yeast replication origin, for example the chromosomal autonomously replicating segment (ars), are retained extrachromosomally within the yeast cell after transformation and are replicated autonomously during mitosis. Also, hybrid vectors that contain sequences homologous to the yeast 2μ plasmid DNA can be used. Such hybrid vectors are integrated by recombination in 2μ plasmids already present within the cell, or replicate autonomously. Suitable marker genes for yeast are especially those that impart antibiotic resistance to the host or, in the case of auxotrophic yeast mutants, genes that complement the host lesions. Corresponding genes impart, for example, resistance to the antibiotic cycloheximide or provide for prototrophy in an auxotrophic yeast mutant, for example the URA3, LEU2, HIS3 or the TRPI gene.

Promoters suitable for expression in yeast are, for example, those of the ADHI, ADHII, or PH05 gene, and also promoters involved in glycolysis, for example the PGK or the GAP promoter.

Optionally, signal sequences which allow the secretion of the TGF-β-like protein can be included in the expression vector. Suitable signal sequences are e.g. derived from the yeast acid phosphatase (PH05) or the yeast invertase gene.

The transformed microbial hosts are cultured in a liquid medium containing assimilatable sources of carbon, nitrogen and inorganic salts, applying methods known in the art.

Various carbon sources are usable. Example of preferred carbon sources are assimilable carbohydrates, such as glucose, maltose, mannitol, fructose or lactose, or an acetate such as sodium acetate, which can be used either alone or in suitable mixtures. Suitable nitrogen sources include, for example, amino acids, such as casamino acids, peptides and proteins and their degradation products, such as tryptone, peptone or meat extracts, furthermore yeast extract, malt extract, corn steep liquor, as well as ammonium salts, such as ammonium chloride, sulphate or nitrate which can be used either alone or in suitable mixtures. Inorganic salts which may be used include, for example, sulphates, chlorides, phosphates and carbonates of sodium, potassium, magnesium and calcium. Additionally, the nutrient medium may also contain growth promoting substances. Substances which promote growth include, for example, trace elements, such as iron, zinc, manganese and the like, or individual amino acids.

The monomeric TGF-β-like protein is recovered from the microbial host cells by methods well known in the art. These methods include lysis or mechanical disruption of the cells in order to release the desired protein, followed by the separation of the TGF-β-like protein from the host cell proteins, e.g. by precipitation and/or chromatographic means.

In cases where the monomeric TGF-β-like protein is produced in the microbial host cells as an insoluble aggregate (inclusion body), it has to be solubilized before being exposed to the refolding conditions. Accordingly, the present invention further relates to a process wherein the monomeric TGF-β-like protein is produced by the steps of:

(a) isolating the water-insoluble protein fraction containing the TGF-β-like protein from the host cells and (b) solubilizing the TGF-β-like protein.

Solubilization and denaturation of the monomer is achieved by acidification of the crude protein suspension containing the monomeric TGF-β-like protein in the non-soluble form to a pH of about 1 to about 4, preferably to about 2.5, optionally in the presence of a reducing agent, such as DTT, or by the addition of chaotropic agents, preferably guanidine HCl or most preferably urea, in a concentration of about 4 to 9M, basic pH or elevated temperatures as described before. The solubilized monomer can be purified from solubilizing chaotropes by dialysis and, if a precipitate occurs during dialysis, by additional centrifugation. The solubilized monomer is chromatographically purified and used for refolding to get the biologically active, dimeric product.

After refolding, the biologically active dimer is purified in order to remove impurities, in particular, pyrogens or other endotoxins which might be present in the preparation after production of the recombinant protein in microbial host cells. Separation of the dimer is performed by chromatography such as sizing gel chromatography, hydrophobic interaction chromatography or ion exchange chromatography, e.g. on a Mono S column and reverse phase HPLC.

The present invention further relates to dimeric biologically active TGF-β-like proteins when produced according to the process of the invention. These TGF-β-like proteins can be used in a variety of therapeutic modalities.

The invention relates further to a monomeric, S-sulfonated TGF-β-like protein, which can be produced by S-sulfonating the monomeric TGF-β-like protein. Monomeric, S-sulfonated TGF-β-like proteins are novel compounds, which can be used for the production of biologically active, dimeric TGF-β-like proteins.

The present invention concerns further a pharmaceutical composition comprising an effective amount of a dimeric, biologically active TGF-β-like protein produced according to the invention, or a pharmaceutically acceptable salt thereof in dosage unit form. Such composition is in the form of infusion solutions or preparations for parenteral, for example intramuscular or intravenous, oral, or especially for local, i.e. topical, administration, respectively. The solutions are preferably isotonic aqueous solutions or suspensions which can be prepared before use, for example from lyophilised preparations which contain the active ingredient alone or together with a pharmaceutically acceptable carrier. Solutions for parenteral use are usually aqueous solutions. They are prepared in conventional manner and may contain in addition to the active ingredient physiological saline, a stabilizer, such as human serum albumin, amino acids, such as arginine or glycine, and a carbohydrate, such as glucose, mannose, dextran or hydroxyethyl starch. The pH may be adjusted with a buffer, e.g. a phosphate, succinate or an amino acid to about 4.5 to 7. Usually the vials are filled with the solution and lyophilized for longer storage.

The compositions contain conventional adjuncts, for example preservatives, stabilisers, wetting agents and/or emulsifiers, solubilisers, salts for regulating the osmotic pressure and/or buffers. The present pharmaceutical compositions, which may, if desired, contain further pharmacologically valuable substances, are produced in a manner known per se, for example by means of conventional mixing, dissolving, lyophilising and/or sterilising processes, and contain from approximately 1 ng to 100 µg/g, especially from approximately 10 ng to 10 µg/g of preparation, and in the case of lyophilisates up to 100%, of the active ingredient.

The TGF-β-like proteins are dual in character in that they on the one hand stimulate the proliferation of certain cell types, namely fibroblasts, and on the other hand inhibit the proliferation of other cell types, namely tumor cells and cells of the immune system.

The dimeric, biologically active TGF-β-like proteins produced according to the invention, optionally in the form of their salts, such as in particular non-toxic pharmaceutical acid addition salts, optionally in form of pharmaceutical formulations, are applied in an effective amount. By the form "effective amount" is intended an amount which exerts a significant healing, e.g. an amount which stimulates the desired cells to grow and which is not toxic to normal cells. This amount can be determined e.g. by in vitro growth experiments. Due to the dual character of TGF-β-like proteins, an "effective amount" is also such which to a significant extent inhibits the growth and proliferation of tumour cells and cells of the immune system. If human or veterinary use is intended, the amount has to be adjusted to the particular tissue to be treated, the mode of application, the severity of the disease, and the age and general condition of the patient to be treated. In general, the either single or daily dosages for adult humans will be in the range of about 0.01 to 20 µg for both the growth stimulating and the inhibiting effect.

The pharmaceutical composition of this invention have a clinical use in the treatment of animals, particularly mammals, more particularly human beings, and, in the case of wound healing, most particularly of old human beings.

The compositions of this invention promote cell migration and proliferation. Since wound healing involves both cell migration and cell proliferation patterns these in vitro findings become directly relevant to the in vivo wound healing process.

Prevention or treatment of bed sores (decubitus ulcers) is a preferred use since they frequently occur in hospital patients, particularly geriatric and wheel chair patients. In elderly people the wound healing process is slower and this group of patients tends to show a higher incidence of wounds (not only decubitus and diabetic ulcers, but trauma, burns and the like) that either heal slowly or do not heal at all.

Two types of application of the compositions of this invention are proposed for both veterinary and, in particular, human medicine.

The first, and preferred application is a topical one for the promotion of surface wound healing, particularly in elderly human beings where the wound healing processes are noticeably slower. There are no limitations as to the type of wound that may be treated, and these include (but are not limited to): Surface ulcers including decubital (bed sore), diabetic, dental, oral, varicose and haemophiliac surface ulcers; burns (especially second and third degree); surgical incisions (including those of dental and cosmetic surgery); accidental wounds (including incisions, penetrations, lacerations and other traumata) and therapeutically induced wounds (including those induced during radiotherapy). When applied topically, the compositions may be combined with other ingredients, such as adjuvants, carriers, solubilizing agents and any other known, or as yet unknown, secondary growth factor(s). Them are no limitations as to the nature of these ingredients except that they must be pharmaceutically and physiologically acceptable for administration and must not degrade the activity, or render harmfully toxic, the active ingredients of the compositions. When the compositions of this invention are applied to surface ulcers, burns, surgical or accidental wounds, the compositions are preferably in the form of a powder, gel, ointment, salve or irrigant, or they may be impregnated into transdermal patches, plasters and bandages, preferably in a liquid or semi-liquid form, or they may be incorporated into a tooth paste or a gum or resin for chewing.

The second application is a systemic one for the healing of internal wounds either following surgery, or damage to the tissues of the inner organs where surgery is either impossible or is not required. Again, there are no limitations as to the type of tissue or wound to be treated and these include (but are not limited to) deep surgical incisions to the inner organs and tissues; bone and cartilage (after fracture); gastric, duodenal and other intestinal ulcers. When applied systemically, the compositions of the invention may be formulated as liquids, pills, tablets, lozenges for enteral administration, or in liquid form for parenteral injection. For the treatment of internal incisions following surgery, they may be in the form of an irrigant, preferably in combination with a physiologically acceptable saline solution. Again, the active ingredients of the compositions may be combined with other ingredients such as adjuvants, carriers, solubilizing agents and any other known, or as yet unknown, secondary growth factor(s). Them are no limitations as to the nature of these ingredients except that they must be pharmaceutically and physiologically acceptable for administration and must not degrade the activity, or render harmfully toxic, the active ingredients of these compositions.

For healing the wounds, the amount of active ingredient to be applied has to be adjusted to the type, severity and location of the wound, and also to the age and general condition of the patient to be treated. In general a single or daily amount of from about 1 µg to 20 µg of TGF-β-like protein per 1 $cm^2$ of wound has already a significant healing effect. For internal use a higher amount should be applied depending on the mode of administration due to the dilution of the TGF-β-like protein in the body fluids.

Further uses of the TGF-β-like proteins produced according to the invention are in bone and tissue repair, treatment of cancer in mammals, as an anti-inflammatory or immunosuppressive agent, as a growth regulator in mammalian cell cultures or as a bone marrow protective agent or mediator of cardioprotection.

EXAMPLES

The following examples illustrate the invention without being meant to be limitative.

Example 1: Cloning and Sequencing of TGF-β1, TGF-β2 and TGF-β3 cDNA

A. Culturing of Cells

Human glioma cells from the CI-215 line (de Muralt, B. et al. (1985) Eur. J. Cancer Clin. Oncol. 21,207) are grown in tissue culture flasks (Falcon T75) containing Dulbecco's Modified Eagle Medium (DMEM, Gibco) and 10% foetal calf serum.

B. RNA Extraction $1 \times 10^8$ cells from the CI-215 human glioma cell line are harvested and Dounce homogenized in 30 ml 5% citric acid with 0.2% (w/v) NP40 detergent at 4° C. The nuclei are separated from the cytoplasm by centrifugation at 2.500 rpm for 10 minutes at 4° C. in a Sorvall RT 6000-B table centrifuge. The supernatant is centfifuged at 15.000 rpm for 30 minutes at 4° C. in a Sorvall RC 5-B centrifuge fitted with a SS-34 rotor. The resulting supernatant is discarded and the pellet is resuspended in 30 ml 0.2M TRIS/HCl (pH 7.5), 5 mM EDTA, 2% SDS, 25.000 units/l Heparin (Sigma), and then extracted 3 times with phenol/chloroform (1:1, v/v), the chloroform consisting of 24 parts chloroform and 1 part isoamylalcohol (v/v). To the final aqueous phase 1 volume 3M sodium acetate (pH 5.0) and 2.5 volumes ethanol are added. The ethanol precipitate is washed twice with 70% ethanol. The RNA pellet is resuspended in 2 ml 10 mM TRIS/HCl (pH 7.5), 1 mM EDTA, 0.05% SDS. Polyadenylated RNA is isolated by oligo-dT cellulose chromatography as described by T. Maniatis in "Molecular Cloning: A Laboratory Manual. Cold Spring Harbor Laboratory, New York (1982)".

C. Synthesis of cDNA

The first strand cDNA is synthesized from 10 μg of poly A$^+$RNA in 100 μl of a solution containing 50 mM TRIS (pH 8.3), 50 mM KCl, 10 mM MgCl$_2$, 1 mM DTT, 30 μg/ml oligo-dT 12–18, 1 mM each dATP, dCTP, dGTP and dTrP, 50 units RNase inhibitor (Promega) and 1000 units of Moloney Leukaemia Virus reverse transcriptase (Gibco-BRL). The reaction is incubated for 1 hour at 37° C. The reaction is then diluted to 400 μl with a second strand buffer containing 20 mM TRIS/HCl (pH 7.5), 5 mM MgCl$_2$, 100 mM KCl, 12.5 units RNase H (Gibco-BRL) are added and the reaction mixture is incubated for 10 minutes at 37° C. The reaction mixture is cooled on ice for 5 minutes and 125 units of E. coli DNA polymerase I (Promega) are added. The reaction mixture is then incubated for a further 2 hours at 16° C. 40 μl 0.5M EDTA are added followed by a phenol/chloroform (1:1, v/v) extraction. To the aqueous phase, 1/10 volume of 3M sodium acetate (pH 6.0) and 4 volumes ethanol are added whereafter the reaction mixture is precipitated for 30 minutes at −70° C.

The ethanol precipitation is centrifuged for 10 minutes at 17.000 g, the pellet is washed twice with 70% ethanol and dried in a Speed-Vac. The double stranded cDNA is dissolved in sterile water and electrophoresed in an agarose gel in TRIS-borate buffer (pH 8.8) to evaluate the size and quantity of the cDNA.

5 μg of the cDNA are then methylated at the EcoRI sites by incubating for 1 hour at 37° C. in 100 μl 50 mM TRIS/HCl (pH 8.0), 0.1 mM EDTA, 80 μM adenosylmethionine and 40 units EcoRI methylase (New England Biolabs). The reaction mixture is extracted with phenol/chloroform and the cDNA is ethanol precipitated and dissolved in sterile water as described above.

5 μg of the cDNA are then prepared for linker ligation by incubating with 20 units of T4 DNA polymerase for 10 minutes at 37° C. in 200 μl 33 mM TRIS-acetate (pH 7.9), 66 mM potassium acetate, 10 mM magnesium acetate, 0.5 mM DTT and 0.1 mM each dATP, dGTP, dCTP and dTTP. The reaction is cooled to room temperature and then 20 units of Klenow Polymerase (Gibco-BRL) are added and incubated for 5 minutes at room temperature and 5 minutes on ice. After adding 10 μl of 0.5M EDTA the reaction mixture is phenol/chloroform extracted and the cDNA is ethanol precipitated and dissolved in sterile water as described above.

12-mer synthetic 5'-phosphorylated linkers (New England Biolabs No. 1070) are then ligated to 5 μg cDNA in 100 μl of a solution containing 10 μg linker in 50 mM TRIS/HCl (pH 7.8), 10 mM MgCl$_2$, 20 mM DTT, 1 mM ATP at 16° C. using 4000 units T4 DNA ligase (New England Biolabs). The ligase is then heat inactivated at 70° C. for 10 minutes, the reaction is diluted to 500 μl in 10 mM TRIS/HCl (pH 7.5), 6 mM MgCl$_2$, 100 mM NaCl and is digested with 1000 units of EcoRI (Boehringer) for 6 hours at 37° C. 50 μl 0.5M EDTA are added and the reaction mixture is heated at 70° C. for 10 minutes. The heated reaction mixture is directly added to a Bio-gel A15M column (200–400 mesh, Bio-Rad) to remove the monomer linker fragments. cDNA of more than 300 bp elutes in the exclusion volume.

D. Cloning into Lambda gt11

Lambda gt11 arms are prepared by digesting 100 μg of lambda vector DNA with EcoRI (New England Biolabs) according to the supplier. The digested DNA is dephosphorylated using 1 unit of Calf Intestine Alkaline Phosphatase from Boehringer Mannheim as described. 20–30 ng of cDNA from the Bio-gel A15M column are coprecipitated in ethanol with 1 μg of gt11 dephosphorylated arms and resuspended in 10 μl of a solution containing 50 mM TRIS/HCl (pH 7.8), 10 mM MgCl$_2$, 20 mM DTT, 1 mM ATP, 15% polyethylene glycol (MW 6000) and 200 units of T4 DNA ligase. The ligation mixture is incubated for 2 hours at 16° C. The reaction mixture is centrifuged for 10 minutes and the pellet is resuspended in 10 μl of sterile water and then in vitro packaged for 3 hours at room temperature according to the supplier (Promega). 0.5 ml of SM phage dilution buffer containing 50 mM TRIS/HCl (pH 7.5), 100 mM NaCl, 100 mM MgSO$_4$ and 0.01% gelatine are added and stabilized with 25 μl of chloroform. A total of 500.000 phages are amplified on 10 YT-plates (15 cm diamter) using 0.7% agarose-YT (Sigma) with E. coli Y 1090 cells as described (Young, R. and Davis, R. (1983) PNAS 80, 1194).

E. Screening and Selection of Clones Containing TGF-β1, TGF-β2 and TGF-β3 Inserts Six replica nylon filters (Cuno) are made from each of the 10 YT-plates and the phages on the filters are denatured with 0.5M NaOH, 1.5M NaCl and neutralized as described in "Molecular Cloning: A Laboratory Manual" (T. Maniatis, Cold Spring Harbour Laboratory, New York, 1982). The filters are placed in 0.2×SSC, 0.2% SDS at 90° C. for 15 minutes and then prehybridized for 4 hours at 45° C. in 2×SSC, 1% SDS, 0.1% ficoll, 0.1% polyvinylpyrrolidone, 0.1% bovine serum albumin, 50 mM NaPO$_4$ (pH 6.8), 50 µg/ml denatured salmon sperm DNA, 0.1 µg/ml oligo A 12–18 and 100 µg/ml poly A$^+$ RNA. Each of the 6 replicas is hybridized overnight at 45° C. in the prehybridization buffer to which one out of six different $^{32}$P-labelled 39 bp oligomers (see below) to a concentration of 2×10$^5$ cpm/ml had been added.

The six oligomers used for hybridization are synthesized on an Applied Biosystem DNA Synthesizer and correspond to the nucleotide sequence encoding either the first amino acids (oligomers 1, 3 and 5) or the last amino acids (oligomers 2, 4 and 6) of the mature forms (112 amino acids) of TGF-β1 (see SEQ ID No. 1), TGF-β2 (see SEQ ID No. 2) and TGF-β3 (see SEQ ID No. 3), respectively.

The two oligomers used for the detection of TGF-β1 sequences are the oligomers having SEQ. ID Nos 4 and 5, respectively, below:

1) 5' GCC CTG GAC ACC AAC TAT TGC TTC AGC TCC ACG GAG AAG 3'

2) 5' TCA GCT GCA CTT GCA GGA GCG CAC GAT CAT GTT GGA CAG 3'

The two oligomers used for the detection of TGF-β2 sequences are the oligomers having SEQ. ID Nos 6 and 7, respectively, below:

3) 5' GCT TTG GAT GCG GCC TAT TGC TTT AGA AAT GTG CAG GAT 3'

4) 5' TTA GCT GCA TTT GCA AGA CTT TAC AAT CAT ATT AGA AAG 3'

The two oligomers used for the detection of TGF-β3 sequences are the oligomers having SEQ. ID Nos 8 and 9, respectively, below:

5) 5' GCT TTG GAC ACC AAT TAC TGC TTC CGC AAC TTG GAG GAG 3'

6) 5' TCA GCT ACA TTT ACA AGA CTT CAC CAC CAT GTT GGA GAG 3'

40 ng each oligomer is labelled at its 3' end using $^{32}$P-dATP and 20 units of terminal transferase (Gibco-BRL) in a 20 µl reaction buffer containing 100 mM potassium cacodylate (pH 7.2), 2 mM CoCl$_2$ and 0.2 mM DTT for 1 hour at 37° C. The reaction mixture is gel filtrated over a Sephadex G-50 column. The eluted labelled oligomers are heated at 95° C. for 5 minutes and added to the prehybridization buffer as described above.

The replicas 1 to 6 are hybridized with oligomers 1 to 6, respectively. After hybridization, the filters are washed twice each with 2×SSC, 1×SSC and 0.1×SSC at room temperature for 15 minutes. Positive plaques are identified by autoradiography and are rescreened by repeating the procedure given above until all of the plaques on the plate are positive. A single plaque is eluted in 1 ml of SM phage dilution buffer (see section 1.D), 100 µl are added to 1 ml E. coli Y 1090 cells and the mixture is kept for 20 minutes at room temperature. The E. coli Y 1090 cells and phages are added to 100 ml YT-medium containing 0.2% maltose and incubated at 37° C. for 7 hours. After adding 1 ml chloroform to the lysed cells, the phage DNA is purified according to the method described in "Molecular Cloning: A Laboratory Manual" (T. Maniatis, Cold Spring Harbour Laboratory, New York, 1982). The purified DNA is dissolved in 1 ml 10 mM TRIS/HCl (pH 7.5), 1 mM EDTA and 100 µl are digested to completion in a total volume of 1 ml with EcoRI following the recommendations of the supplier (Boehringer). The enzyme reaction is phenol/chloroform extracted and ethanol precipitated. The EcoRI cDNA inserts are purified by gel electrophoresis (Ultrapure BRL) using NA-45 DEAE paper (Schleicher and Schuell). The DNA is eluted in 50 mM TRIS/HCl (pH 7.5), 5 mM EDTA, 1M NaCl, phenol/chloroform extracted and ethanol precipitated. The resulting pellet is washed twice with 70% ethanol and resuspended in 10 mM TRIS/HCl (pH 7.5), 1 mM EDTA.

F. Sequencing of cDNA Inserts

The EcoRI cDNA inserts are subcloned into Bluescript KS$^+$ Vector (Stratagene). The cDNA identity is confirmed by double-stranded sequencing according to the method described by F. Sanger et al. (1977) PNAS 74,5463 using the above oligomers (see section 1.E) and a Sequenase kit (U.S. Biochemicals). The nucleotide sequence covering the 112 amino acids of the mature TGF-β1, TGF-β2 and TGF-β3 are depicted under SEQ ID No. 1, 2 and 3, respectively.

G. Amplification of cDNA Inserts and Subcloning into Plasmid PGem-5

The above oligomers (see section 1.E) for identifying TGF-β1, TGF-β2 and TGF-β3 sequences are used to amplify the cDNA inserts encoding the mature 112 amino acids forms (including the stop codon).

The EcoRI cDNA inserts of the Bluescript KS$^+$ plasmids (see section 1.F) are gel purified as described above (see section 1.E). 50 ng of each cDNA insert are amplified in the presence of 2×2 µg of the respective two oligomers by a polymerase chain reaction in a 100 µl reaction mixture containing 10 mM TRIS/HCl (pH 8.35), 50 mM KCl, 1.5 mM MgCl$_2$, 0.05% (w/v) NP-40, 0.05% (w/v) Tween 20 and 200 µm of each dATP, dGTP, dCTP and dTTP using 5 units Taq Polymerase (Perkin-Elmer Cetus). 30 rounds of amplification are performed under the following temperatures using a Perkin-Elmer Cetus Heating Block: 93° C./0.1 minutes, 55° C./0.2 minutes, 71° C./1.5 minutes. The resulting 339 bp fragments covering the coding sequences of TGF-β1, TGF-β2 and TGF-β3, respectively, are gel purified and subcloned into plasmid PGem-5ZF(+) (Promega) digested with NcoI, dephosphorylated with Calf Intestinal Alkaline Phosphatase (Boehringer) and filled in with Klenow polymerase (Gibco-BRL). The resulting constructs are designated as pGKM 125 (TGF-β1), pGKM 740 (TGF-β2) and pGKM 126 (TGF-β3) and are used to transform competent E. coli Y 1090 cells (see example 2). Clones carrying the correct inserts encoding TGF-β1, TGF-β2 and TGF-β3 are designated as E. coli Y1090/pGKM 125 (TGF-β1), E. coli Y1090/pGKM 740 (TGF-β2) and E. coli Y1090/pGKM 126 (TGF-β3), respectively.

Example 2: Expression of TGF-β1, TGF-β2 and TGF-β3 in E. coli

A. General Methods

Bacterial strain (E. coli K12):

LC 137: htpR$_{am}$, lon$_{R9}$, lac$_{am}$, mal$_{am}$, trp$_{am}$, pho$_{am}$, rspL, tsx::Tn10, supC$_{ts}$ (Goff, S. A. et al. (1984) PNAS 81, 6647–6651).

Plasmids:

pPLMu: (Buell, G. et al. (1985) Nucleic Acids Res. 13, 1923–1938). This plasmid carries the bacteriophage λP$_L$ promoter with the phage Mu ner gene ribosome binding site (Van Leerdam, E. et al. (1982) Virology 123, 19–28).

pcI$_{857}$: Plasmid encoding a thermolabile λCI$_{857}$ repressor and conferring resistance to kanamycin (Remault, E. et al. (1983) Gene 22, 103–113).

SDS gel-electrophoresis:

SDS polyacrylamide gel-electrophoresis (SDS-PAGE) and protein staining is done as described previously (Laemmli, U. K. (1970) Nature 227, 680–685) using the Miniprotean II cell from BIORAD and 1 mm thick 18% polyacrylamide gels.

Heat induction:

7 ml of LB-Medium (Maniatis et al. (1982), Molecular Cloning, Cold Spring Harbor Laboratory, New York) in a 20 ml culture tube containing 40 µg of each ampicillin and kanamycin (LB/amp/kan) are inoculated with a single colony and incubated with shaking overnight at 30° C. 5 ml of this overnight culture are added to 15 ml of LB/amp/kan in a 100 ml Erlenmeyer flask. This flask is transferred to a 42° C. waterbath shaker. A 2 ml sample is taken before transfer (non-inducing conditions) and 1 ml samples at 1 hour intervals after the transfer (inducing conditions). Cells are pelleted by centrifugation (5 min, 10,000 rpm in an Eppendorf centrifuge) and the supernatant is discarded. The pellet is resuspended in 100 gl of sample buffer for SDS-PAGE and heated for 10 min at 95° C. 5 µl aliquots are loaded for SDS-PAGE.

Preparation of competent cells:

Competent E. coli cells are prepared by the calcium chloride procedure as described in Maniatis et al. (1982), Molecular Cloning, Cold Spring Harbor Laboratory, New York. Cells carrying plasmid pcI857 are grown at 30° C.

B. Construction of Expression Vectors pPLMu.hTGF-β1, pPLMu.hTGF-β2 and pPLMu.hTGF-β3 and Expression of TGF-β1, TGF-β2 and TGF-β3

E. coli Y1090/pGKM 125, E. coli Y1090/pGKM 740 and E. coli Y1090/pGKM 126 (see example 1.G) cells are grown in LB medium and plasmid DNA is prepared by the method of Birnboim, H. C. and Doly, H. (1979) Nucleic Acids Research 7, 1513. 5 µg of plasmid DNA are cut to completion in 50 µl restriction buffer with either NcoI and SalI (pGKM125), NcoI and EcoRV (pGKM740) or NcoI alone (pGKM126) following the recommendations of the supplier (Boehringer). The DNA is precipitated by addition of 5 µl 3M sodium acetate, 100 mM $MgCl_2$, 5 mM EDTA and 150 µl ethanol. After incubation at −70° C. for 15 min the DNA is pelleted by centrifugation at 13,000 g for 15 min in a SS34 rotor in a Sorvall centrifuge. The supernatant is discarded and the pellet is resuspended in 80 µl 0.089M TRIS borate, 0.089M boric acid and 0.002M EDTA (TBE buffer) containing 0.25% bromphenol blue and 0.25% xylene cyanol. 4 times 20 µl samples are electrophoresed through a 1% agarose gel in TBE buffer containing 0.5 µg/ml ethidium bromide at 50 volts till the bromphenol blue marker reaches the bottom of the 10 cm long and 0.8 cm thick gel. The DNA fragments coding for mature TGF-β1, TGF-β2 and TGF-β3, respectively, are visualized under short wave UV light, cut out with a razor blade and electroeluted from the gel piece in a Schleicher & Schüll Biotrap apparatus applying 200 mamp for 1.5 hours. The eluted DNA fragments are precipitated (see above) and resuspended in 20 µl TE.

5 µl of plasmid pPLMu are linearized by digestion with either NcoI and SalI, NcoI and EcoRV or NcoI alone and gel purified as described above for the fragment DNAs. 100 ng of the linearized and purified pPLMu vector DNA and 3 times the molar equivalent of the respective purified fragment DNA are incubated at 4° C. for 15 hours in 20 µl of ligation buffer (70 mM TRIS/HCl, pH 7.5, 10 mM $MgCl_2$, 5 mM DTT, 0.1 mM adenosine-triphosphate) containing 1 unit of DNA ligase (Boehringer).

10 µl of the ligation mixture are added to 200 µl of cold (4° C.) competent E. coli LC 137 cells carrying plasmid $pcI_{857}$. After 30 min the cells are heat shocked by incubation for 1.5 min in a 42° C. water bath. 2 ml of LB medium are added and the culture is shaken for 60 min at 30° C. 200 µl aliquots are plated on LB plates containing ampicillin and kanamycin and incubated for 22 hours at 30° C. Single colonies are cultivated and plasmid DNA is analysed. Subcloning of the DNA fragments coding for TGF-β1, TGF-β2 and TGF-β3 in pPLMu results in plasmids pPLMu.hTGF-β1, pPLMu.hTGF-β2 and pPLMu.hTGF-β3, respectively. Clones containing the above constructs are referred to as E. coli LC 137/pPLMu.hTGF-β1, E. coli LC 137/pPLMu.hTGF-β2 and E. coli LC 137/pPLMu.hTGF-β3, respectively.

E. coli LC 137/pPLMu.hTGF-β1, E. coli LC 137/pPLMu.hTGF-µ2 and E. coli LC 137/pPLMu.hTGF-β3 cells are heat induced (see example 2.A) and the expressed proteins are analysed by SDS-PAGE. TGF-β1, TGF-β2 and TGF-β3 all appear as heat induced proteins 2 hours after heat induction migrating with an apparent molecular weight of approximately 12.000 D.

C. Fermentation of Transformants

Overnight cultures of E. coli LC 137/pPLMu.h.TGF-β1, E. coli LC 137/pPLMu.h. TGF-β2 and E. coli LC 137/pPLMu.h.TGF-β3 in 2 l Erlenmeyer flasks containing 750 ml of LB medium with 40 mg/l of ampicillin and kanamycin are grown at 30° C. 300 ml of the overnight cultures are added to 750 ml of LB medium containing antibiotics as mentioned above in 2 l Erlenmeyer flasks and heated to 42° C. by shaking for approximately 3.5 minutes in a 65° C. water bath. The flasks are then transferred to a 42° C. shaker and incubated for 3 hours. The flasks are cooled down to 12° C. in an ice water bath and the cells are collected after centrifugation for 10 minutes at 8,000 rpm in a GSA rotor (Sorvall).

Example 3: Expression of TGF-β1, TGF-β2 and TGF-β3 in Saccharomyces cerevisiae

The coding sequences of mature TGF-β1, TGF-β2 and TGF-β3 are expressed in Saccharomyces cerevisiae under the control of the inducible promoter of the yeast acid phosphatase (PH05).

The expression vectors are constructed in two steps:

A. construction of plasmid pJDB207/PH05-RIT 12,

B. construction of plasmids pJDB207R/PH05-TGF-β1, pJDB207R/PH05-TGF-β2 and pJDB207R/PH05-TGF-β3, where A) provides the yeast vector and the PH05 transcriptional terminator and B) provides the expression cassettes with an insert coding for mature TGF-β1, TGF-β2 and TGF-β3, respectively, under the control of the PH05 promoter.

A. Construction of plasmid pJDB207/PH05-RIT 12

Plasmid p31RIT 12 (European patent application EP 277.313) is linearized with restriction endonuclease SalI. Partial HindIII digestion in the presence of ethidium bromide results in a 1 kb SalI/HindIII fragment comprising the 276 bp SalI/BamHI pBR322 sequence, the 534 bp promoter of the yeast acid phosphatase PH05, the yeast invertase signal sequence (coding for 19 amino acids) and the PH05 transcriptional terminator. The 1 kb SalI/HindIII fragment of p31RIT 12 is cloned in to the yeast-E.coli shuttle vector pJDB207 (Beggs, J. D. in: Molecular Genetics in yeast, Alfred Benzon Symposium 16, Copenhagen, 1981, pp. 383-389), which had been cut with SalI and HindIII. The resulting plasmid containing the 1 kb insert is referred to as pJDB207/PH05-RIT 12.

B. Construction of plasmid pJDB207R/PH05-TGF-β2

Plasmid pGKM740 (TGF-β2) (see example 1.G) is cut with NcoI. The sticky ends are filled in a reaction with Klenow DNA polymerase. EcoRI linker (5'-CCGGAATTCCGG; Biolabs) are added and the mixture is ligated. The resulting circular plasmid is referred to as pGKMA668 (TGF-β2) and is cut with EcoRI and SalI. A 0.4 kb EcoRI/SalI fragment is isolated from an agarose gel, purified and resuspended in sterile water at a concentration of 25 μg/ml. The fragment contains the mature coding sequence of TGF-β2 with an ATG in frame to codon GCT which defines amino acid Ala 1 of mature TGF-β2.

The PH05 promoter is isolated from plasmid p31RIT 12 (see above) on a 534 bp BamHI/EcoRI fragment. Plasmid pJDB207/PH05-RIT 12 is cut with BamHI and XhoI. The large, 6.8 kb BamHI/XhoI fragment is isolated. The PH05 transcriptional terminator remains on the fragment. The BamHI/EcoRI PH05 promoter fragment, the EcoRI/SalI fragment coding for TGF-β2, and the BamHI/XhoI vector fragment are ligated. One correct clone with the TGF-β2 gene under the control of the PH05 promoter cloned in an anticlockwise orientation into pJDB207 is referred to as pJDB207R/PH05-TGF-β2.

In an analogous manner, mature TGF-β1 and TGF-β3 are expressed in *S. cerevisiae*. The plasmids containing the coding sequences of TGF-β1 and TGF-μ3 are pGKM125 and pGKM126, respectively (see example 1.G). After digestion of these plasmids with NcoI, addition of EcoRI linkers and ligation, the resulting circular plasmids are cut with EcoRI and SalI. The EcoRI/SalI fragments are cloned into pJDB207 as described above. The resulting plasmids are referred to as pJDB207R/PH05-TGF-β1 and pJDB207R/PH05-TGF-β3.

C. Transformation of *S. cerevisiae* Strain GRF18

*Saccharomyces cerevisiae* strain GRF18 (MATα, his3-11, his3-15, leu2-3, leu2-112, can$^R$, DSM 3665) is transformed with plasmids
pJDB207R/PH05-TGF-β1
pJDB207R/PH05-TGF-β2
pJDB207R/PH05-TGF-β3
using the transformation protocol described by Hinnen, A. et al. (1978) PNAS 75, 1929. Transformed yeast cells are selected on yeast minimal medium plates deficient in leucine. Single transformed yeast colonies are isolated and referred to as
*Saccharomyces cerevisiae* GRF18/pJDB207R/PH05-TGF-β1
*Saccharomyces cerevisiae* GRF18/pJDB207R/PH05-TGF-β2 and
*Saccharomyces cerevisiae* GRF18/pJDB207R/PH05-TGF-β3.

D. Fermentation of *S. cerevisiae* Transformants and Preparation of Cell Extracts The yeast transformants, as mentioned above, contain plasmids with PH05 promoter-controlled expression cassettes and therefore require derepression of the promoter for the expression of TGF-β1, TGF-β2 or TGF-β3. Transformants are each grown in two successive precultures (10 ml and 50 ml) in yeast high $P_i$ minimal medium prepared according to the recipe of the Difco Yeast Nitrogen Base without amino acids but containing 10 g/l L-asparagine instead of $(NH_4)_2SO_4$, 1 g/l L-histidine and 20 g/l glucose. The cells of the second preculture are washed in 0.9% NaCl and all the cells are used to inoculate 100 ml of low $P_i$ minimal medium prepared according to the recipe of the Difco Yeast Nitrogen Base medium (without amino acids), but containing 0.03 g/l $KH_2PO_4$, 10 g/l L-asparagine, 1 g/l L-histidine and 20 g/l glucose. The cultures are agitated at 30° C. at 180 rpm.

Cells from 10 ml of culture are collected at 5 h, 24 h and 48 h by centrifugation at 3000 rpm and washed once in 0.9% NaCl. The cell pellet is resuspended in lysis buffer [66 mM potassium phosphate pH 7.4, 4 mM Zwittergent (Calbiochem)]. 8 g of glass beads (0.5–0.75 mm in diameter) are added and the suspension is shaken vigerously 4–5 times for 2 min each on a Vortex Mixer in the cold. The cell extract is decanted to get rid of the glass beads. Cell debris in the extract are sedimented by centrifugation for 5 min at 3000 rpm at 4° C. The supernatant and pellets are separated and stored at −20° C.

Example 4: Production of Dimeric, Biologically Active TGF-β1, TGF-β2 and TGF-β3

The procedures given below for the production of dimeric, biologically active TGF-β2 can be applied in analogy for the recovery of dimeric, biologically active TGF-β1, TGF-β3, and other "TGF-β-like proteins", respectively.

A. Recovery of Non-Soluble, Monomeric TGF-β2 from *E. coli*

*E. coli* LC 137/pPLMu.hTGF-β2 cells are fermented as described in example 2.C. Cell disruption and recovery of non-soluble TGF-β2 is performed at 4° C. About 18 g of wet cells are suspended in 60 ml of 0.1M TRIS/HCl, 10 mM EDTA, 1 mM PMSF (Phenyl Methan Sulphonyl Fluoride), pH 8.3 (disruption buffer). The cells are passed two times through a Frenchpress (SLM Instruments, Inc.) according to the manufacturers instructions and the volume is brought to 200 ml with the disruption buffer. The suspension is centrifuged for 20 min at 15,000 g. The pellet obtained is suspended in 100 ml disruption buffer containing 1M NaCl and centrifuged for 10 min as above. The pellet is suspended in 100 ml disruption buffer containing 1% Triton X-100 (Pierce) and again centrifuged for 10 min as above. The washed pellet is then suspended in 50 ml of 20 mM Tris/HCl, 1 mM EDTA, 1 mM PMSF, 1% DTT and homogenised in a Teflon tissue grinder. The resulting suspension contains crude monomeric TGF-β2 in a non-soluble form.

B. Solubilization and Purification of Monomeric TGF-β2

10 ml of the TGF-β2 suspension obtained according to example 4.A or 4. C are acidified with 10% acetic acid to pH 2.5 and centrifuged in an Eppendorf centrifuge for 10 min at room temperature. The supernatant is chromatographed on a Sephacryl S-100 column (Pharmacia, 2.6×78 cm) in 10% acetic acid at a flow rate of 1.4 ml/min. (Alternatively, the chromatography can be performed on Sephacryl S-100 HR (Pharmacia) and the column can be run in 1% acetic acid or 5 mM HCl, respectively.) Fractions containing monomeric, denatured TGF-β2 eluting between 190 min and 220 min are pooled. This material is used for refolding to get biologically active, dimeric TGF-β2 (examples 4.G.J.K.L) or for further purification for structural analysis (example 4.D.).

C. Recovery of Monomeric TGF-β2 from *Saccharomyces cerevisiae*

The pellet of broken cells obtained from a 500 ml fermentation performed as described in example 3.D is suspended in 20 ml 4M urea, 0.1M TRIS, 1% DTT, pH 8.0. The mixture is kept at room temperature for 30 minutes with intermittant vortexing every 5 minutes. Insoluble material is removed by centrifugation at 30,000 g for 30 minutes at 4° C. and the supernatant is adjusted to pH 2.5 with acetic acid and dialysed extensively against 5% acetic acid overnight at 4° C. The solution is centfifuged as above and the clear supernatant is concentrated by ultrafiltration on a YM 10 membrane (Amicon) to a final volume of 4 ml. The sample is then chromatographed on Sephacryl S-100 HR (Pharmacia) in 5% acetic acid as described in example 4.B yielding monomeric TGF-β2.

D. Further Purification of Monomeric TGF-β2 by RP-HPLC

Aliquots of the pooled fractions from the Sephacryl S-100 column (example 4.B) are purified on a Vydac 214TP5415 HPLC reverse phase column (4.6×150 mm, The Separations Group, Hesperia, Calif., USA). The column is equilibrated in a mixture of 70% TFA 0.1% in water and 30% TFA 0.08% in acetonitrile, and the product is eluted by a linear gradient over 30 min ending with a mixture of 55% TFA 0.1% in water and 45% TFA 0.08% in acetonitrile at a flow rate of 1 ml/min. The eluate is monitored for absorbance at 216 nm and individual peaks are collected manually according to the UV absorbance. Denatured, monomeric TGF-β2 is eluted at 21.5 min. Depending on the individual reverse phase column used for the separation the same preparation of TGF-β2 is eluted around 16 min and 18 min, respectively.

TGF-β2 fractions are analysed by RP-HPLC using the same column and solvent system as above. TGF-β2 is eluted by a linear gradient over 42 min starting from 100% TFA 0.1% in water and ending with a mixture of 30% TFA in water and 70% TFA 0.08% in acetonitrile. TGF-β2 is eluted as a single peak after 30.4 min. Depending on the individual column used retention times of 29 min and 29.9 min, respectively, are obtained. TGF-β2 is analyzed after admixture of chemically reduced natural porcine TGF-β2 (British Biotechnology Limited, Oxford, UK) which has an identical primary structure as human TGF-β2 (Marquardt, H. et al. (1987) J. Biol. Chem. 262, 12127–12131). The mixture elutes as a single peak confirming the identity of the material.

E. Analysis of Monomeric TGF-β2 by SDS-PAGE

Individual aliquots of the Sephacryl S-100 column (example 4.B) or the reverse phase column (example 4.D) are dried in vacuo and analysed by SDS-PAGE (Laimmli, U. K. (1970) Nature 227, 680) on 15% polyacrylamide slab gels stained with Coomassie Blue R-250. A single band of an apparant molecular weight of about 12,000 D is obtained which is indistinguishable from reduced natural porcine TGF-β2.

F. N-Terminal Amino Acid Sequence Determination of Monomeric TGF-β2

TGF-β2 from example 4.B is evaporated in vacuo, dissolved in 25 µl acetic acid and subjected to amino acid sequence determination on a gas phase protein sequencer model 470A (Applied Biosystems).

The N-terminal amino acid sequence is shown by SEQ ID No. 10 below:

$$\underset{}{Ala}-\underset{}{Leu}-\underset{}{Asp}-\underset{}{Ala}-\underset{5}{Ala}-\underset{}{Tyr}-\underset{}{X}-\underset{}{Phe}-\underset{}{Arg}-\underset{10}{Asn}-\underset{}{Val}-$$
$$\underset{}{Gln}-\underset{}{Asp}-\underset{}{Asn}-\underset{15}{X}-\underset{}{X}-\underset{}{Leu}-\underset{}{Arg}-\underset{}{Pro}$$

wherein X denotes an amino acid not positively identified.

Similarly, the N-terminal amino acid sequence is determined for the 4-vinylpyridine derivative of TGF-β2 prepared as described by Marquardt, H. et al. (1987) J. Biol. Chem. 262, 12127–12131.

The N-terminal amino acid sequence is shown by SEQ ID No. 11 below:

Ala—Leu—Asp—Ala—Ala—Tyr—Cys—Phe—Arg—Asn—Val—
Gln—Asp—Asn—X—Cys—Leu—Arg—Pro—Leu—Tyr—Ile—
Asp—Phe—X—Arg—Asp—Leu— wherein X denotes an amino acid not positively identified. Cysteine was determined as S-pyridylethylcysteine.

G. Generation of Dimeric, Biologically Active TGF-β2

3 mg of monomeric denatured TGF-β2 from example 4.B is dissolved in 140 ml 50 mM Tris/HCl pH 8.0, 1M NaCl, 5 mM EDTA, 2 mM reduced glutathione, 1 mM oxidised glutathione and 33 mM Chaps (Calbiochem). After 72 hours at 4° C. the pH of the solution is adjusted to pH 2.5 with HCl and the mixture is concentrated 10 times by ultrafiltration on a YM 10 membrane (Amicon, Danvers, Mass., USA) in an Amicon stirred cell. The concentrated solution is diluted to the original volume with 10 mM HCl and concentrated to a final volume of 10 ml by the same method. The precipitate formed is removed by centrifugation at 5000 g for 30 minutes. The supernatant contains disulfide linked dimeric TGF-β2 as judged by SDS-PAGE under non-reducing conditions. The biological activity of the preparation is measured by the cell migration and growth assay (example 5.A) and the cell growth inhibition assay (example 5.B).

Alternatively, instead of using monomeric TGF-β2, the S-sulfonated TGF-β2 derivative (example 4.M) is used for the generation of dimeric active TGF-β2 by applying essentially the procedure described in this example with the exception of the sodium chloride concentration which is 2M. Purification and isolation of the dimeric TGF-β2 is performed with the same methods as dimeric TGF-β2 generated from the underivatised monomeric protein (example 4.H and 4.I).

H. Isolation of Dimeric TGF-β2 by Cation Exchange Chromatography on a Mono S Column The concentrated solution from example 4.G is applied at a flow rate of 1 ml/min onto a Mono S HR 5/5 column (Pharmacia) equilibrated in a mixture of 85% buffer A (20 mM sodium acetate, 30% isopropanol, pH 4.0) and 15% buffer B (buffer A containing 1M sodium chloride). The column is then washed at the same flow rate keeping the buffer mixture composition constant until the absorbance reading at 280 nm has reached baseline level, followed by a linear gradient over 20 minutes starting upon injection at the equilibration conditions and ending with a mixture of 50% buffer A/50% buffer B. Dimeric biologically active TGF-β2 is eluted 9 minutes after the start of the gradient and collected manually. As judged by biological activity determination, SDS-PAGE under non-reducing conditions and RP-HPLC no dimeric TGF-β2 was found in the flow through fraction. Additionally, no monomeric TGF-β2 was detected by SDS-PAGE in the dimeric TGF-β2 peak eluted from the column by the salt gradient.

I. Further Purification of Dimeric TGF-β2

Dimeric TGF-β2 from example 4.G is diluted with the same volume of 0.1% TFA in water and subjected to RP-HPLC on a Vydac 214TP5415 column (4.6×150 mm, The Separations Group, USA) equilibrated in a mixture of 80% TFA 0.1% in water and 20% TFA 0.08% in acetonitrile. The column is eluted by a linear gradient over 40 min starting upon injection at the equilibration conditions and ending with a mixture of 60% TFA 0.1% in water and 40% TFA 0.08% in acetonitrile at a flow rate of 1 ml/min. The eluate is monitored for absorbance at 216 nm. TGF-β2 is eluted with a retention time of 32.7 min and collected manually. SDS-PAGE analysis under non reducing conditions revealed a single sharp band of apparent molecular weight of about 25 kD. The obtained dimeric TGF-β2 is of high purity.

J. Alternative Method I for the Generation of Dimeric, Biologically Active TGF-β2

Monomeric TGF-β2 from example 4.B is dissolved at a concentration of 0.1 mg/ml in 50 mM sodium phosphate, pH 8.0, 2M NaCl, 5 mM EDTA, 2.5 mM cysteine, 1 mM cystine and 50 mM Chaps (Calbiochem). After 300 hours at 4° C. the pH is adjusted to pH 2.5 with 10% TFA. Then 30 mg/ml of Sepralyte C-1 (preparative grade, 40 μm, Analytichem International, Harbor City, Calif., USA), pretreated sequentially with 0.1% TFA in acetonitrile and 0.1% TFA in water, is added and the mixture is gently stirred for 30 min at room temperature. The gel is filtered over a glass frit covered with fresh prewashed Sepralyte C-1 (20% the amount added to the refolding solution). The gel is washed first with (5 times the gel volume) buffer A (0.2M NaCl/0.1% TFA/water), then with a mixture of 80% buffer A and 20% buffer B (0.08% TFA in acetonitrile). TGF-β2 is eluted with a mixture of 70% buffer A and 30% buffer B. The eluate is applied directly onto a Mono S column HR 5/5 (Pharmacia). Purification and isolation of TGF-β2 is performed as in examples 4.H and 4.I, respectively.

Alternatively, acetonitrile in buffer A and buffer B, respectively, used for washing the Sepralyte C-1 gel and elution of TGF-β2 is replaced by isopropanol. Washing is then performed with a mixture of 90% buffer A and 10% buffer B and elution of TGF-β2 is achieved with a stepwise gradient (steps of 2% buffer B) starting with a mixture of 80% buffer A and 20% buffer B and ending with a mixture of 70% buffer A and 30% buffer B. Further procedure is as in examples 4.H and 4.I, respectively.

K. Alternative Method II for the Generation of Dimeric, Biologically Active TGF-β2

Monomeric TGF-β2 from example 4.B is dissolved at a concentration of 0.5 mg/ml in 100 mM Tris/HCl, pH 8.5, 1M NaCl, 5 mM EDTA, 1 mM reduced glutathione, 1 mM oxidised glutathione and 50 mM Chaps (Calbiochem). After 450 hours at 4° C. the mixture is adjusted to pH 4.0 with acetic acid, diluted by addition of 7 volumes of 20 mM sodium acetate, pH 4.0 and pumped onto a Mono S column HR 5/5 (Pharmacia). Further procedure as in example 4.H and 4.I, respectively.

L. Alternative Method III for the Generation of Dimeric, Biologically Active TGF-β2 Using Thioredoxin as a Disulfide Promoting Agent Monomeric TGF-β2 from example 4.B is dissolved at a concentration of 0.025 mg/ml in 100 mM Tris/HCl, pH 8.0, 50 mM Chaps, 0.05 mg/ml thioredoxin. The mixture is incubated at 4° C. for 24 hours. As determined by the cell migration and growth assay (example 5.A) the yield of refolded dimeric active TGF-β2 is similar to that of the method described in example 4.G. Purification and isolation of dimeric TGF-β2 is as in examples 4.H and 4.I. TGF-β2 is separated from thioredoxin by the Mono S column of example 4.H.

M. Preparation of S-Sulfonated TGF-β2 and Its Use for the Generation of Dimeric, Biologically Active TGF-β2

Monomeric TGF-β2 from example 4.B is dissolved at room temperature in 6M urea, 100 mM Tris/HCl, pH 8.0, 50 mM sodium sulfite and 0.2 mM cysteine. Formation of S-sulfonated TGF-β2 is monitored by RP-HPLC using the conditions of example 4.D. The retention time of S-sulfonated TGF-β2 is 31.8 min. After completion of the reaction, the pH of the solution is adjusted to pH 2.0 with 1N HCl. S-sulfonated TGF-β2 is desalted on a FPLC "Fast Desalting Column" HR10/10 (Pharmacia) in 10 mM HCl. Refolding of S-sulfonated TGF-β2 to give dimeric active TGF-β2 is done essentially according to the procedure of example 4.G.

N. Recyclisation of Incorrectly Folded TGF-β2

Solid guanidinium hydrochloride and DTT is added to the material not bound to the Mono S column of example 4.H to give a concentration of 6M and 5 mM, respectively, and the pH is adjusted to pH 8.5 with solid Tris. After 1 hour at room temperature the mixture is subjected to RP-HPLC using the same column and solvent system as in example 4.D. Reduced monomeric TGF-β2 is collected, and acetonitrile is removed in the vacuum. This preparation is then subjected to the refolding procedure of example 4.G either directly or together with newly isolated monomeric TGF-β2 from example 4.B or 4.C, thus improving the total yield of refolded active dimeric TGF-β2.

O. Generation of Heterodimeric, Biologically Active TGF-β

Heterodimeric TGF-βs consisting of two different disulfide-linked polypeptide chains of 112 amino acids each can be prepared by subjecting equimolar amounts of the two respective monomers to refolding conditions as described in example 4.G. Purification and isolation of the dimers is performed according to examples 4.H and 4.I allowing the separation of the heterodimeric form from the homodimers.

P. Peptide Mapping and Sequence Determination of Monomeric TGF-β1, TGF-β2 and TGF-β3, respectively

TGF-β2:

92 μg (6.7 nmoles) S-pyridylethylated recombinant TGF-β2 described in example 4.F. are dried in an vaccum centrifuge and redissolved in 200 μl 5 mM HCl. 200 μl 0.2M Tris-acetate buffer, pH 7.8, containing 10 mM Zwittergent 3–12 detergent (Calbiochem Corporation, La Jolla, Calif.) is added and mixed with the protein solution. The cleavage is carried out with 2 μg (dissolved in 50 μl water) endoproteinase Asp-N (from Pseudomonas fragi mutant, Sequence Grade, Boehringer Mannheim Biochemica, FRG) at 37° C. After 13 hours, 50 µl 10% (v/v) TFA are added and the mixture is separated by RP-HPLC on a C4 narrow-bore column (Vydac 214TP52, 2.1×250 mm) with a linear gradient of 5 to 40% (v/v) acetonitrile in 0.1% TFA/water in 35 min at a flow rate of 0.1 ml/min and UV detection at 216 nm. The collected peaks are analysed by plasma desorption mass spectroscopy as described in example 4.S.

The comparison of the measured molecular mass (in Daltons, D) of the peptides in their protonated form (M+H$^+$) with the calculated molecular mass allows the following identification (the following Peptide Sequences are designated SEQ ID Nos 12–20, respectively):

| Retention Time (min) | M + H$^+$ (D) | Calculated Mass M(D) | Peptide Sequence |
|---|---|---|---|
| 16.1 | 566.1 | 564.6 | DFKR |
| 23.9 | 1832.3 | 1831.1 | NTINPEASASPCCVSQ |
| 25.9 | 1292.5 | 1291.5 | DAAYCFRNVQ |
| 29.0 | 1307.7 | 1306.6 | DNCCLRPLY |
| 31.2 | 1320.0 | 1318.5 | DTQHSRVLSLY |
| 32.1 | 1421.1 | 1419.7 | DNCCLRPLYI |
| 33.0 | 3132.3 | 3131.5 | DTQHSRVLSLYNTINPEASASPCCVSQ |
| 36.9 | 3425.3 | 3424.9 | DLGWKWIHEPKGYNANFCAGACPYLWSS |
| 44.5 | 3739.5 | 3739.5 | DLEPLTILYYIGKTPKIEQLSNMIVKSCKCS |

TGF-β1:

32 µg (2.5 nmoles) S-pyridylethylated recombinant TGF-β1 (prepared similarly as S-pyridylethylated recombinant TGF-β2) are cleaved with 1.5 µg endoproteinase Lys-C using the same procedure as for the digestion of TGF-β2 except that the incubation time is 9 h and a linear gradient of 12 to 27% acetonitrile in 90 min is used on a C18 column (Vydac 218TP5205, 2.1×50 mm) (the following Peptide Sequences are designated SEQ ID Nos 21–28, respectively).

binant TGF-β2) are digested with 0.4 µg endoproteinase Asp-N as described for TGF-β2 except that the incubation time is 22.5 hours and the separation is carried out on a C18 column (Vydac 218TP5205, 2.1×50 mm) with a linear gadient of 16 to 32% acetonitrile in 80 min (the following Peptide Sequences are designated SEQ ID Nos 29–39, respectively).

| Retention Time (min) | M + H$^+$ (D) | Calculated Mass M(D) | Peptide Sequence |
|---|---|---|---|
| 9.4 | 810.6 | 808.9 | WIHEPK |
| 13.2 | 619.2 | 617.7 | DLGWK |
| 20.4 | 1584.6 | 1583.7 | ALDTNYCFSSTEK |
| 34.9 | 1613.3 | 1611.9 | VEQLSNMIVRSCK |
| 50.6 | 1869.8 | 1868.3 | NCCVRQLYIDFRK |
| 79.8 | 2875.2 | 2874.3 | GYHANFCLGPCPYIWSLDTQYSK |
| 87.1 | 4189.1 | 4189.0 | VLALYNQHNPGASAAPCCVPQALEPLPIVYYVGRKPK |
| 89.8 | 3965.0 | 3963.7 | VLALYNQHNPGASAAPCCVPQALEPLPIVYYVGRK |

TGF-β3:

20 µg (1.46 nmoles) S-pyridylethylated recombinant TGF-β3 (prepared similarly as S-pyridylethoxylated recom-

| Retention Time (min) | M + H$^+$ (D) | Calculated Mass M(D) | Peptide Sequence |
|---|---|---|---|
| 7.9 | 1308.0 | 1306.6 | ENCCVRPLY |
| 8.8 | 1381.0 | 1379.5 | DTNYCFRNLE |
| 11.6 | 1205.5 | 1206.3 | DTTHSTVLGLY |
|  | 1252.4 | 1250.4 | DTNYCFRNL |

-continued

| Retention Time (min) | M + H⁺ (D) | Calculated Mass M(D) | Peptide Sequence |
|---|---|---|---|
| 19.4 | 1421.5 | 1421.5 | DTTHSTVLGLYNT |
| | 1551.2 | 1551.9 | DLEPLTLYYVGR |
| 36.5 | 3030.4 | 3029.4 | DTTUSTVLGLYNTLNPEASASPC CVPQ |
| 39.8 | 2782.6 | 2781.2 | DTNYCFRNLEENCCVRPLYI |
| 45.6 | 3457.3 | 3456.0 | DLGWKWVHEPKGYYANFCSGPCPYL RSA |
| 77.9 | 3726.5 | 3725.5 | DLEPLTELYYVGRTPKVEQLSNMV VKSCKCS |
| 82.6 | 6736.9 | 6736.9 | DTMSTVLGLYNTLNPEASASPCC VPQDLEPLTEIYYVGRTPKVEQL SNMVVKSCKCS |

Q. Structural Characterisation of Monomeric TGF-β2 Expressed in *Saccharamyces cerevisiae*

An aliquot of the material from example 4.C is further purified by RP-HPLC as described in example 4.D and the N-terminal amino acid sequence is determined as described in example 4.F.

The amino acid sequence is shown by SEQ ID No. 40 below:

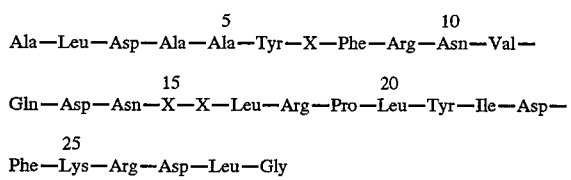

wherein X denotes an amino acid not positively identified.

R. Refolding of Monomeric TGF-β2 Expressed in *Saccharamyces cerevisiae* and Isolation and Characterisation of Dimeric TGF-β2

Refolding of the monomeric TGF-β2 expressed in *Saccharomyces cerevisiae* and isolation of dimeric biologically active TGF-β2 is performed as described in example 4.G, 4.H and 4.I respectively.

S. Molecular Mass of Dimeric TGF-β2

An aliquot of 6 μg monomeric TGF-β2 and of 20 μg dimeric biologically active TGF-β2 obtained in example 4.D and 4.I, respectively is dissolved in 25% acetic acid, adsorbed on nitrocellulose and analysed on a BIO ION 20 Plasma Desorption Mass Spectrometer (Applied Biosystems, Uppsala, Sweden). The molecular masses determined are

| | |
|---|---|
| M = 12,738.0 | for monomeric TGF-β2 (calculated Mass M = 12,719.7) |
| M = 25,422.0 | for dimeric TGF-β2 (calculated Mass M = 25,421.2 assuming all cysteins as disulfides) |

T. Molecular Mass of Dimeric TGF-β3

Dimeric biologically active TGF-β3 is prepared similarly to TGF-β2 described in examples 4.A, 4.B, 4.G, 4.H and 4.I. The molecular mass of dimeric biologically active TGF-β3 is determined as described in example 4.S. The molecular mass found is:

| | |
|---|---|
| M = 25,434.0 | (calculated Mass M = 25,427.2 assuming all cysteins as disulfides) |

Example 5: In Vitro Activity Test for TGF-β1, TGF-μ2 and TGF-β3

A. Cell Migration and Growth Assay

The assay is based on the chemotactic activity of TGF-β on fibroblasts (Postlethwaite, A. E. et al. (1987) J. Exp. Med. 165, 251) and is performed as described by Burk, R. (1973) PNAS 70, 369.

The cell migration promoting activity of TGF-β1, TGF-β2 and TGF-β3 is assayed by measuring the number of normal Balb/c 3T3 fibroblasts which migrate over a culture period of 22 hours into a wounded monolayer culture of said cells in serum-free medium (Dulbecco's Modified Eagle Medium, Gibco) containing TGF-β1, TGF-β2 or TGF-β3, respectively, as compared to the number of fibroblasts which migrate into a wounded monolayer culture in the absence of TGF-β.

The growth promoting activity of TGF-β1, TGF-β2 and TGF-β3 is determined by the stimulatory effect on cellular DNA synthesis and cell division. This activity is apparent in said monolayer cultures observed under the light microscope after a culture period of 44 hours and is quantified by either (a) counting the number of cell nuclei, in any given field of view, in cultures of said cells grown in serum-free medium containing TGF-β1, TGF-β2 or TGF-β3, respectively, as compared to the number of cell nuclei counted, in any given field of view, in cultures grown in the absence of TGF-β, or (b) measuring the amount of radio-labelled ³H-thymidine uptake in cultures of said cells grown in serum-free medium containing TGF-β1, TGF-β2 or TGF-β3, respectively, as compared to the amount of 3H-thymidine uptake in cultures grown in the absence of TGF-β.

In these dose response experiments concentrations of the completely purified TGF-β1, TGF-β2 and TGF-β3 proteins (see example 4.K) in the range of 0.1 to 1000 pg per milliliter of culture medium are sufficient to elicit 50% of the maximal migration and growth promoting response.

B. Cell Growth Inhibition Assay

The colorimetrical assay is based on the inhibitory effect of TGF-β on the growth of human A 375 melanoma cells (Brown, T. J. et al. (1987) J. Immunol. 139, 2977). TGF-β1, TGF-β2 and TGF-β3 samples are serially diluted (1:3) in flat bottomed 96-well tissue culture plates (Falcon) containing RPMI-1640 medium (Gibco) and 5% foetal calf serum. Control wells receive medium alone. $1.5 \times 10^4$ A375 melanoma cells are added to each well. After a 72 hours incubation period at 37° C. in 5% $CO_2$, the A375 cell monolayers are washed once, fixed and stained with crystalviolet for 15 minutes. Unbound stain is washed out intensively. The stained cells are lysed with 33% acetic acid to release the stain (which is confined to the cell nuclei) and the OD was measured at 590 nm with a multiskan-8 Channel Photometer equipped with an Olivetti M 24 PC to calculate the activity of the test compounds. Since the intensity of staining in each well is directly related to the number of nuclei (and therefore to the number of cells), this technique provides a colorimetrical assay for measuring the anti-proliferative effects of TGF-β1, TGF-β2 and TGF-β3 molecules.

Treatment with purified TGF-β1, TGF-β2 and TGF-β3 over a concentration range of 0.001 to 10 nM inhibits the growth of A375 melanoma cells.

Example 6: In Vivo Activity Tests for Refolded TGF-β1, TGF-β2 and TGF-β3

A. Healing of Partial-Thickness Wounds in Old Mice

It is recognised that wound healing processes become impaired with advancing age (Grove, G. L. (1982) Arch. Dermatol. Res. 272:381) and therefore represent major problems in the field of geriatric medicine. Therefore, the in vivo biological effects of the refolded active dimeric TGF-βs on the healing of partial-thickness wounds (formed by second degree burning) are investigated in a partially deficient or impaired wound repair situation, namely in old animals, using the following protocol similar to the one described by Schultz, G. S. et al. (1987) Science 235:350.

Single middermal thermal injuries are made on the dorsal thorax of anaesthetized old C57/BL6 mice (aged 450 days or more), whose backs have been previously shaved and depilitated with a commercial cream-type hair remover, by a single 10 second application of a brass template (1×1 cm, 8 gm) which has been equilibrated at 80° C. in a water bath. The resulting blister is surgically removed and the burns are treated daily, for 5 days, with a topical application of 25 µl sterile vehicle buffer solution (consisting of 0.8% w/v Hydroxypropyl cellulose in a solution of 10 mM Histidine, 140 mM NaCl, pH 7.4) containing various amounts (500 ng, 100 ng or 10 ng) of the refolded active dimeric TGF-β form, or with buffer solution alone, or are left untreated. All topically applied materials are sterile, endotoxin-free and pyrogen-free, and all mice are individually caged for the duration of the experiment. Each experimental group consists of 5 animals.

After 5 days of treatment with TGF-β, the mice are anaesthetized, the blisters (if present) are surgically removed from the burns, and the burns are photographed. Areas of burns that have regenerated epithelium are outlined onto uniform thickness transparent overhead projector film and the percentage of each original burn area that has healed is calculated by planimetry. Results are also compared with the epithelial regeneration process in young (56–84 day old) C57/BL6 mice with identical middermal burns which are left untreated for the duration of the experiment.

An example of such an experiment using refolded dimeric active TGF-β2 is shown in the following table where values shown represent the mean and range of group evaluations.

| Group | Animals | TGF-β2 dose per incision (ng) | % age of original burn area healed on day 6 |
|---|---|---|---|
| 1 | Old | 500 | 59 ± 8 |
| 2 | Old | 100 | 55 ± 6 |
| 3 | Old | 10 | 46 ± 7 |
| 4 | Old | Buffer Only | 10 ± 9 |
| 5 | Old | Untreated | 16 ± 6 |
| 6 | Young | Untreated | 66 ± 9 |

The results of the planimetrical analyses shown in the above table demonstrate that topical application of refolded active dimeric TGF-β2 daily for 5 days in a suitable vehicle buffer stimulates and accelerates epithelial regeneration in partial-thickness wounds on old mice in a dose dependant fashion (Groups 1–3) when compared with vehicle buffer only or untreated wounds (Groups 4 & 5 respectively). Young mice are apparently competent enough to successfully re-epithelialize their wounds in the absence of any topically applied TGF-β (Group 6). Histological analyses reveal the extent of the enhanced re-epithelialization process together with a hyperkeratosis of the regenerated epidermis on Day 6 in the TGF-β-treated wounds.

B. Healing of Full-Thickness Wounds in Adult Rats

The biological effects of refolded active dimeric TGF-βs are also investigated in a second in vivo model of wound repair, namely on the healing of full-thickness wounds (formed by surgical incisioning) in adult rats, using the following protocol similar to the one described by Mustoe, T. A. et al. (1987) Science 237:1333.

Single, full-thickness 5 cm long linear incisions are made with surgical scissors 1.5 cm on both sides of the dorsal midline of pentobarbitone anaesthetized male Wistar rats (300–350 g) whose backs have been previously shaved and depilitated with a commercial cream-type hair remover. In the experimental groups, edges of the left side incisions (as viewed with the dorsal side uppermost) receive single topical applications (100 µl) of a sterile vehicle buffer (consisting of 0.8% w/v Hydroxypropyl cellulose in a solution of 10 mM Histidine, 140 mM NaCl, pH 7.4) containing various amounts (2 µg, 1 µg, 0.1 µg or 0.01 µg) of a refolded active dimeric TGF-β form. Edges of the contralateral right side incisions receive corresponding equal amounts of a placebo control (Bovine Serum Albumin) in the said vehicle buffer and edges of incisions in control animals receive vehicle buffer alone in the left side incisions and no treatment in the right side incisions following surgical incisioning. All topically applied materials are sterile, endotoxin-free, and pyrogen-free. Edges of each wound are then coapted with 5 evenly placed, interrupted horizontal mattress sutures of 5-0 Ethilon. All animals are caged separately and the wounds are left to heal for varying periods up to and including 21 days post treatment. After sacrifice the entire dorsal skin is removed from each animal and all subcutaneous fat is carefully dissected from the underside of each of the skins using a surgical scalpel. A template consisting of two parallel surgical blades (8 mm distance between blades) is then used to excise strips of skin (between sutures on each incision) for tensile strength measurements. Samples are taken from one end of each incision for histological analysis. The maximum load tolerated by each excised skin sample is measured with a Universal Tensile Strength Machine Model 144501 (Zwick, Ulm, FRG). Measurements are made on 30 mm×8 mm strips which are secured between hydraulic clamps and then stretched to breaking point at a rate 10 mm per minute, with the maximum load recorded on a chart recorder. Measurements are made on triplicate samples from each wound and experimental groups consisted of 4 animals. Breaking strength is not measured on wounds showing evidence of infection or excessive haemorrhaging (less than 3% of all wounds).

An example of such an experiment using refolded dimeric active TGF-β2 is shown in the following table where values shown represent the average ratios of tensile strength between TGF-β2-treated wounds and placebo-treated wounds at 3 equally spaced timepoints over a 21 day day time period.

| Group | TGF-β2 dose per incision (μg) | Ratio of Tensile Strength TGF-β: Placebo Treatment at | | |
|---|---|---|---|---|
| | | Day 7 | Day 14 | Day 21 |
| 1 | 2.00 | 1.9:1 | 1.7:1 | 1.4:1 |
| 2 | 1.00 | 1.8:1 | 1.4:1 | 1.3:1 |
| 3 | 0.10 | 1.4:1 | 1.3:1 | 1.2:1 |
| 4 | 0.01 | 1.2:1 | 1.1:1 | 1.0:1 |
| 5 | None* | 1.0:1 | 1.0:1 | 1.0:1 |

(*ratio of vehicle buffer only v no treatment)

The results of the tensile strength measurements shown in the above table demonstrate that a single topical application of refolded active dimeric TGF-β2 in a suitable vehicle buffer enhances the breaking strength up to 2 fold, and accelerates the healing, of full-thickness incisional wounds in adult rats in a dose dependent fashion over a 21 day time period (Groups 1–4) when compared against the control group (Group 5). Histological analyses reveal the marked increase influx of mononuclear cells, fibroblasts and collagen production in TGF-β-treated wounds over the 21 day period as compared to control wounds. A transient hyperkeratosis is also evident in TGF-β-treated wounds up to 14 days after the treatment.

C. Wound Chamber Implant Model in Adult Rats

The biological effects of refolded active dimeric TGF-βs are also investigated in a third in vivo model of wound repair, namely on the cellular ingrowth, vascularization and formation of fibrous granulation tissue in and around porous chamber implants in adult rats, based on a protocol similar to the one described by Spore, M. B. et al., (1983) Science 219:1329.

Empty rigid polytetrafluoroethylene tubes (internal and external diameters, 10 and 12 mm respectively; length 32 mm), each perforated by apporixmately 250 regularly spaced holes (diameter 1 mm) and sealed at each end with a removable cap of identical material, are gas sterilized and surgically inserted sub-cutaneously, in symmetrical fashion, through small incisions into the dorsal flanks of pentobarbitone anaesthetized adult Wistar rats (350–400 g). One gas-sterilized tissue cage is implanted into each flank and the incisions are closed with single surgical clips (Clay-Adams Auto-Clips, 9 mm) which are removed 5 days after surgery. Following surgical insertion the chambers become encapsulated with fibrous connective tissue although there is a relative absence of cells within the chambers themselves. This model provides a sterile, defined and enclosed space within each chamber where various parameters of a wound healing response can be quantitated. Animals are used for experimentation 14 days after implantation of the chambers, after full healing of the surgical incision.

At this time daily injections of 100 μl sterile vehicle buffer solution (consisting of 0.5% w/v Hydroxypropyl cellulose in a solution of 10 mM Histidine, 140 mM NaCl, pH 7.4) containing various amounts (1 μg, 0.1 μg or 0.01 μg) of a refolded, active dimeric TGF-β form are given directly into the left side chambers (as viewed with the dorsal side uppermost). Right side chambers receive corresponding equal amounts of a placebo control (Bovine Serum Albumin) in the said vehicle buffer. Control animals receive vehicle buffer alone in the left side chambers whereas right side chambers remain untreated for the duration of the experiment. Experimental groups consist of 5 animals. Injections are made once daily for 5 days and all injected materials are sterile, endotoxin-free and pyrogen-free. All animals are individually caged for the duration of the experiment and are sacrificed 24 hr after the last series of injections. Chambers are then removed from each animal by aseptic technique, and the fibrous tissue from inside each chamber is 'wet' weighed. The total serous protein in the chamber fluid is estimated using the method of Lowry et al., (1951) J. Biol. Chem. 193:265. Samples of fibrous tissue removed from inside and outside each chamber are prepared for histological analysis. Sterility of the chamber contents is checked by incubation of chamber fluid samples on brain/heart infusion plates for 72 hr at 37° C. Measurements are not made on chambers showing evidence of infection or rejection (less than 3% of all chambers).

An example of such an experiment using refolded dimeric active TGF-β2 is shown in the following table where values shown represent the average ratios of measurements obtained for protein in 5 matched pairs of chambers (left v right) from each group of animals.

| Group | TGF-β2 dose per left chamber (μg) | Ratio of protein in matched chambers (left:right) | |
|---|---|---|---|
| | | Fibrous Tissue | Serous Protein |
| 1 | 1.00 | 3.0:1 | 1.5:1 |
| 2 | 0.10 | 2.5:1 | 1.4:1 |
| 3 | 0.01 | 2.1:1 | 1.3:1 |
| 4 | None* | 1.0:1 | 1.0:1 |

*ratio of vehicle buffer only v no treatment

The results of the protein measurements shown in the above table demonstrate that local injection of refolded active dimeric TGF-β2 daily for 5 days in a suitable vehicle buffer enhances, up to 3 fold, the accumulation of total fibrous tissue, in a dose-dependant manner, in left-sided chambers as compared to the right-sided contralateral chambers which have received corresponding equal amounts of a placebo protein. A small dose-dependent increase in the amount of serous protein in left-sided chambers is also observed following multiple injection with TGF-β2 (Groups 1–3). No differences are apparent between left-sided and right-sided chambers in the control group (Group 5).

On post-mortem biopsy of animals in Groups 1–3 it is consitently observed that the left-sided TGF-β-treated chambers are more firmly attached to the surrounding connective tissue of the body wall than the contralateral right-sided chambers that have received placebo injections. Furthermore, histological analyses show that the thickness and vascularity of the fibrous tissue surrounding the TGF-β-treated chambers is markedly greater than that of the tissue surrounding the placebo-treated chambers. Sheets of migrating fibroblasts and mononuclear cells are also evident within the fibrous tissue inside TGF-β-treated chambers. No apparent differences are observed in either the thickness or vascularity of the fibrous tissue surrounding the chambers, nor in the degree of attachment of chambers to the connective tissue of the body wall in the control group (Group 4). These results suggest that the diffusion of TGF-β from the chamber is responsible for the observed differences in effect.

A sterile infiltrate of inflammatory cells, consisting predominantly of macrophages, is found in the serous fluid of TGF-β-treated chambers, whereas contralateral placebo-treated chamber fluid shows a predominance of polymorphonuclear leukocytes. The contents of all 40 chambers in Groups 1–4 shown in the Example are found to be sterile after incubating samples of the chamber contents on brain/heart infusion for 72 hr at 37° C.

Example 7: Pharmaceutical Composition

A. Cream

| Ingredients: | % (v/v) |
| --- | --- |
| Sorbitan monostearate | 2.0 |
| Polyoxyethylene sorbitan monostearate | 3.0 |
| Cetyl alcohol | 5.0 |
| Light liquid paraffin | 8.0 |
| Isopropyl myristate | 2.0 |
| Active substance, TGF-β-like protein | $1.0 \cdot 10^{-5}$ |
| Propylene glycol | 2.0 |
| Glycerin | 2.0 |
| Deionised water | 76.0 |
| Preservatives and other stabilizers | q.s. |

Heat the aqueous phase to 55°–60° C., dissolve the active substance in it, and disperse the melted lipid phase in it by vigorous stirring. Cool to toom temperature and homogenize.

In a similar manner a cream comprising 0.01 to 20 μg/ml, respectively, can be produced.

Of this cream 100 μl/cm² of wound is applied.

B. Ointment

| Ingredients: | % (v/v) |
| --- | --- |
| Sorbitan trioleate | 5.0 |
| Wax, microcrystalline | 3.0 |
| Light liquid paraffin | 9.0 |

B. Ointment -continued

| Ingredients: | % (v/v) |
| --- | --- |
| Isopropyl myristate | 10.0 |
| Lanolin alcohols | 3.0 |
| Active substance, TGF-β-like protein | $1.0 \cdot 10^{-5}$ |
| Propylene glycol | 2.0 |
| Glycerin | 2.0 |
| Magnesium sulphate, hydrous | 0.7 |
| Deionised water | 65.3 |
| Preservatives | q.s. |

Dissolve the active substance in the aqueous phase, with gentle heating, and disperse the solution in the melted lipid phase. Cool to room temperature and homogenize.

In a similar manner an ointment comprising 0.01 to 20 μg/ml, respectively, can be produced. Of this ointment 100 μl/cm² of wound is applied.

C. Parenteral Solution

| Ingredients: | |
| --- | --- |
| Active Substance, TGF-β-like protein | 0.05 mg/ml |
| ± Human Serum Albumin | 1 mg/ml |
| Arginine or Glycine | 20 mg/ml |
| ± Carbohydrate | 5–20 mg/ml |
| pH | 7 |

The carbohydrate is glucose, mannose, dextran, hydroxyethyl starch or a mixture thereof.

The pH is adjusted with phosphate, succinate, amino acids or a mixture thereof.

Vials with 0.05 mg TGF-β-like protein/0.5 ml are made and lyophilised.

Deposition of microorganisms

The following microorganisms were deposited at the Deutsche Sammlung yon Mikroorganismen (DSM), Mascheroder Weg 1b, D-3300 Braunschweig (FRG):

| microorganismus | deposition date | accession number |
| --- | --- | --- |
| E. coli LC 137/pPLMu.hTGF-β1 | November 28, 1989 | DSM 5656 |
| E. coli LC 137/pPLMu.hTGF-β2 | November 28, 1989 | DSM 5657 |
| E. coli LC 137/pPLMu.hTGF-β3 | November 28, 1989 | DSM 5658 |
| Saccharomyces cerevisiae GRF 18 | March 4, 1986 | DSM 3665 |

We claim:

1. A process for the production of a dimeric, biologically active form of a recombinantly produced Transforming Growth Factor type β (TGF-β)-like protein selected from the group consisting of TGF-β2, TGF-β3, heterodimeric TGF-β2, heterodimeric TGF-β3, bone morphogenic protein (BMP)-2, and salts thereof, consisting essentially of adding a solubilized, denatured, unfolded, monomeric form of said TGF-β-like protein to a solution containing a low molecular weight sulfhydryl/disulfide redox system and a mild detergent selected from the group consisting of 3-(3-chlolamidopropyl)dimethylammonio-1-propanesufonate, 3-(3-chlolamidopropyl)dimethylammonio-2-hydroxyl-1-propanesulfonate, digitonin, cholate and deoxycholate in a concentration which permits folding of the monomeric TGF-β-like protein into the spatial conformation while retaining said protein in soluble form, which after dimerization, has biological activity, and recovering the dimeric, biologically active TGF-β-like protein.

2. The process according to claim 1 in which the monomeric form of said TGF-β-like protein is produced by the steps of:

(a) culturing a microbial host comprising a nucleotide sequence encoding the TGF-β-like protein linked in the proper reading frame to an expression control sequence such that said protein is expressed, and (b) recovering the TGF-β-like protein in a denatured, monomeric, soluble form.

3. The process according to claim 2 wherein the monomeric TGF-β-like protein is expressed as an insoluble aggregate in the microbial host cells and wherein the process further comprises the steps of:

(a) isolating the insoluble aggregate containing the TGF-β-like protein from the host cells and (b) solubilizing the TGF-β-like protein.

4. The process according to claim 2 in which the microbial host is a yeast or a bacterium.

5. The process according to claim 2 in which the nucleotide sequence encodes a protein selected from the group consisting of human TGF-β2 and TGF-β3.

6. The process according to claim 3 in which the insoluble aggregate is solubilized at a pH of about 1 to about 4 and in which the resulting monomer of the TGF-β-like protein is purified by chromatography.

7. The process according to claim 6 in which the insoluble aggregate of the TGF-β-like protein is solubilized at a pH of about 2.5.

8. The process according to claim 3 in which the insoluble aggregate is solubilized with a chaotropic agent.

9. The process according to claim 8 in which the chaotropic agent is urea or guanidine -HCl.

10. The process according to claim 9 in which the chaotropic agent is present in a concentration of about 4 to about 9M.

11. The process according to claim 1 which the sulfhydryl/disulfide redox system is selected from the group consisting of glutathione in its oxidized and reduced form, dithiotreitol in its oxidized and reduced form, β-mercaptoethanol in its oxidized and reduced form, cystine and its reduced form, and cystamine and its reduced form.

12. The process according to claim 11 wherein the sulfhydryl/disulfide redox system is at a concentration of about 1 to 100 mM and wherein the molar ratio of the oxidized and the reduced form is between 100:1 and 1:100.

13. The process according to claim 1 in which the sufhydryl/disulfide redox system is glutathione in its oxidized and reduced form.

14. The process according to claim 13 in which the sulfhydryl/disulfide redox system is present at a concentration of about 1 to about 10 mM and wherein the molar ratio of the oxidized and the reduced form is between 6:1 and 1:6.

15. The process according to claim 1 in which the low molecular weight sulfhydryl/disulfide redox system is replaced by thioredoxin or disulfide isomerase at a concentration of about 10 to 1000 µg/ml.

16. The process according to claim 15 in which the low molecular weight sulfhydryl/disulfide redox system is replaced by thioredoxin at a concentration of about 50 to 200 µg/ml.

17. The process according to claim 1 in which the sulfhydryl/disulfide redox system is glutathione in its oxidized and reduced form at a concentration of about 1 to 10 mM, wherein the molar ratio of the oxidized and the reduced form is 1:1 to 1:2, and in which the solubilizing agent is 3-(3-chlolamidopropyl)dimethylammonio-1-propanesulfonate at a concentration of about 30 mM to 60 mM.

18. The process according to claim 1 in which the mild detergent is 3-(3-chlolamidopropyl)dimethylammonio-1-propanesufonate.

19. The process according to claim 18 in which the mild detergent is 3-(3-chlolamidopropyl)dimethylammonio-1-propanesufonate at a concentration of about 1 to 100 mM.

20. The process according to claim 1 in which the refolding conditions additionally comprise metal ions.

21. The process according to claim 20 in which the metal ions are $Cu^{2+}$ or $Fe^{3+}$.

22. The process according to claim 21 in which the metal ions are present at a concentration of about 0.01 to about 100 µM.

23. The process according to claim 1 in which the refolding is perfomred at a pH of about 6 to about 10 and at a temperature of about 0° C. to about 37° C.

24. The process according to claim 1 wherein the pH is about 8.

25. The process according to claim 1 in which additionally $O_2$ is bubbled through the buffer system.

26. The process according to claim 1 in which the, biologically active TGF-β-like protein obtained is purified by chromatography.

27. The process according to claim 1 wherein said TGF-β-like protein is selected from the group consisting of TGF-β2, TGF-β3, BMP-2 and a salt thereof.

28. A process according to claim 1, in which the monomeric TGF-β-like protein is S-sulfonated prior to refolding.

29. A process according to claim 1, in which the detergent is selected from the group consisting of 3-(3-chlolamidopropyl)dimethylammonio-1-propanesulfonate and 3-(3-chlolamidopropyl)dimethylammonio-2hydroxy-1-propanesulfonate.

30. The process according to claim 1 wherein the concentration of the mild detergent is about 1 mM to about 100 mM.

* * * * *